(12) United States Patent
Jönsson

(10) Patent No.: US 10,926,065 B2
(45) Date of Patent: Feb. 23, 2021

(54) MEDICAL DEVICE, METHOD AND SYSTEM FOR TEMPORARY OCCLUSION OF AN OPENING IN A LUMEN OF A BODY

(71) Applicant: AEEG AB, Helsingborg (SE)

(72) Inventor: Anders Jönsson, Bromma (SE)

(73) Assignee: AEEG AB, Helsingborg (SE)

( * ) Notice: Subject to any disclaimer, the term of this patent is extended or adjusted under 35 U.S.C. 154(b) by 137 days.

(21) Appl. No.: 16/241,544

(22) Filed: Jan. 7, 2019

(65) Prior Publication Data

US 2019/0134358 A1 May 9, 2019

Related U.S. Application Data

(63) Continuation of application No. 13/063,926, filed as application No. PCT/EP2009/061982 on Sep. 15, 2009, now abandoned.
(Continued)

(30) Foreign Application Priority Data

Sep. 15, 2008 (SE) .................................. 0850015-9

(51) Int. Cl.
*A61M 25/10* (2013.01)
*A61B 17/12* (2006.01)
(Continued)

(52) U.S. Cl.
CPC ..... *A61M 25/1002* (2013.01); *A61B 17/1204* (2013.01); *A61B 17/1215* (2013.01);
(Continued)

(58) Field of Classification Search
CPC ............ A61M 25/104; A61M 25/1002; A61M 29/02; A61B 17/12036; A61B 17/1204;
(Continued)

(56) References Cited

U.S. PATENT DOCUMENTS 4,909,252 A 3/1990 Goldberger
5,069,662 A * 12/1991 Bodden ............... A61M 1/3621
604/101.05
(Continued)

FOREIGN PATENT DOCUMENTS

DE 101 02 045 A1 1/2003
JP 2001269410 10/2001
(Continued)

*Primary Examiner* — Tuan V Nguyen
(74) *Attorney, Agent, or Firm* — Inskeep IP Group, Inc.

(57) ABSTRACT

A medical system is disclosed that has three basic components; a retractable sheet, a first balloon that has a centrally arranged hollow, and a collapsible/expandable support structure at the hollow. The first balloon is for instance mounted/molded onto the exterior surface of the support structure. The aggregate of support structure and the first balloon is positioned, and once the sheet has been retracted from the first balloon, the first balloon is inflated. The support structure may be self-expandable or expandable by an expansion unit, such as a further balloon arranged at its inside. The lumen of the support structure is chosen to be smaller than that of a main lumen. The outside diameter of the inflated first balloon is chosen to be larger than the interior diameter of the main lumen.

2 Claims, 11 Drawing Sheets

Related U.S. Application Data

(60) Provisional application No. 61/097,315, filed on Sep. 16, 2008.

(51) Int. Cl.
*A61M 29/02* (2006.01)
*A61B 17/00* (2006.01)
*A61B 17/22* (2006.01)
*A61F 2/01* (2006.01)
*A61M 25/00* (2006.01)
*A61M 39/24* (2006.01)

(52) U.S. Cl.
CPC .. *A61B 17/12036* (2013.01); *A61B 17/12045* (2013.01); *A61B 17/12104* (2013.01); *A61B 17/12109* (2013.01); *A61B 17/12118* (2013.01); *A61B 17/12136* (2013.01); *A61B 17/12145* (2013.01); *A61B 17/12172* (2013.01); *A61B 17/12177* (2013.01); *A61M 25/104* (2013.01); *A61M 29/02* (2013.01); *A61B 2017/0061* (2013.01); *A61B 2017/00597* (2013.01); *A61B 2017/00783* (2013.01); *A61B 2017/00867* (2013.01); *A61B 2017/22054* (2013.01); *A61F 2/013* (2013.01); *A61M 2025/0024* (2013.01); *A61M 2025/1052* (2013.01); *A61M 2025/1097* (2013.01); *A61M 2039/2406* (2013.01); *A61M 2039/246* (2013.01); *A61M 2039/2466* (2013.01)

(58) Field of Classification Search
CPC ........ A61B 17/12045; A61B 17/12104; A61B 17/12109; A61B 17/12118; A61B 17/12136; A61B 17/12145; A61B 17/1215; A61B 17/12172; A61B 17/12177

See application file for complete search history.

(56) References Cited

U.S. PATENT DOCUMENTS

| | | |
|---|---|---|
| 5,470,314 A | 11/1995 | Walinsky |
| 5,728,131 A | 3/1998 | Frantzen et al. |
| 6,139,517 A | 10/2000 | Macoviak et al. |
| 6,168,616 B1 | 1/2001 | Brown, III |
| 6,183,492 B1 | 2/2001 | Hart et al. |
| 6,409,750 B1 | 6/2002 | Hyodoh et al. |
| 6,443,982 B1 | 9/2002 | Israel et al. |
| 6,599,267 B1 | 7/2003 | Ray et al. |
| 7,850,643 B1 | 12/2010 | Pacetti |
| 2002/0026230 A1 | 2/2002 | Moll et al. |
| 2004/0064089 A1 | 4/2004 | Kesten et al. |
| 2006/0212112 A1 | 9/2006 | Evans et al. |
| 2006/0259119 A1 | 11/2006 | Rucker |
| 2006/0287701 A1 | 12/2006 | Pal |
| 2007/0067010 A1 | 3/2007 | Wang et al. |
| 2009/0112184 A1* | 4/2009 | Fierens ............... A61M 1/3613 604/509 |
| 2012/0059447 A1 | 3/2012 | Zilla et al. |

FOREIGN PATENT DOCUMENTS

| | | |
|---|---|---|
| WO | WO 00/12169 | 3/2000 |
| WO | WO 2008/058017 A | 5/2008 |

* cited by examiner

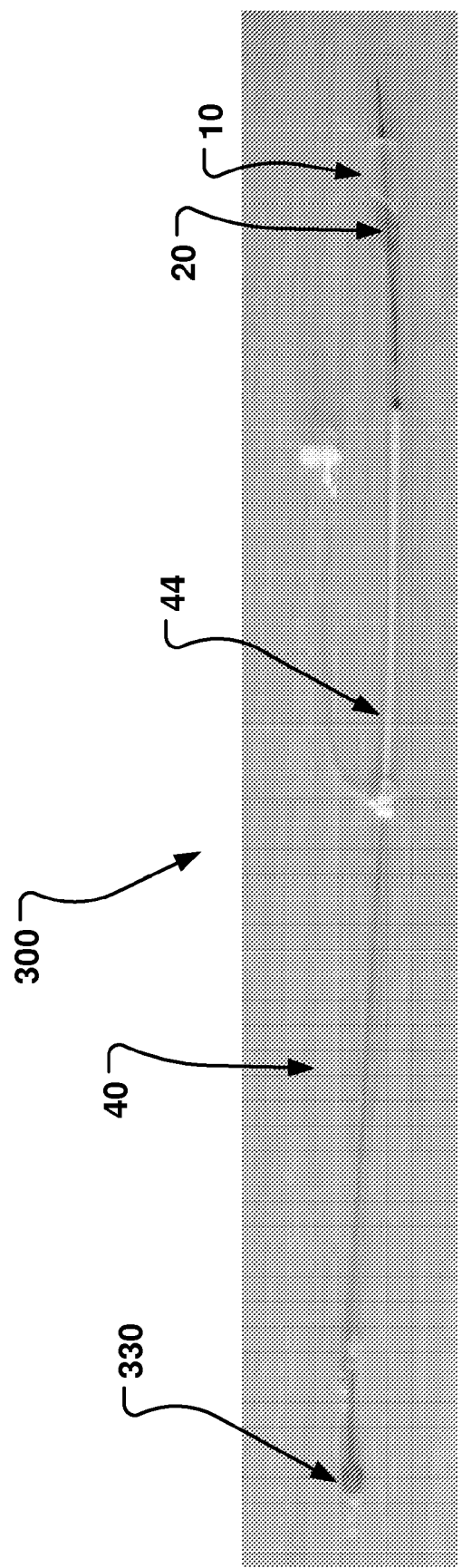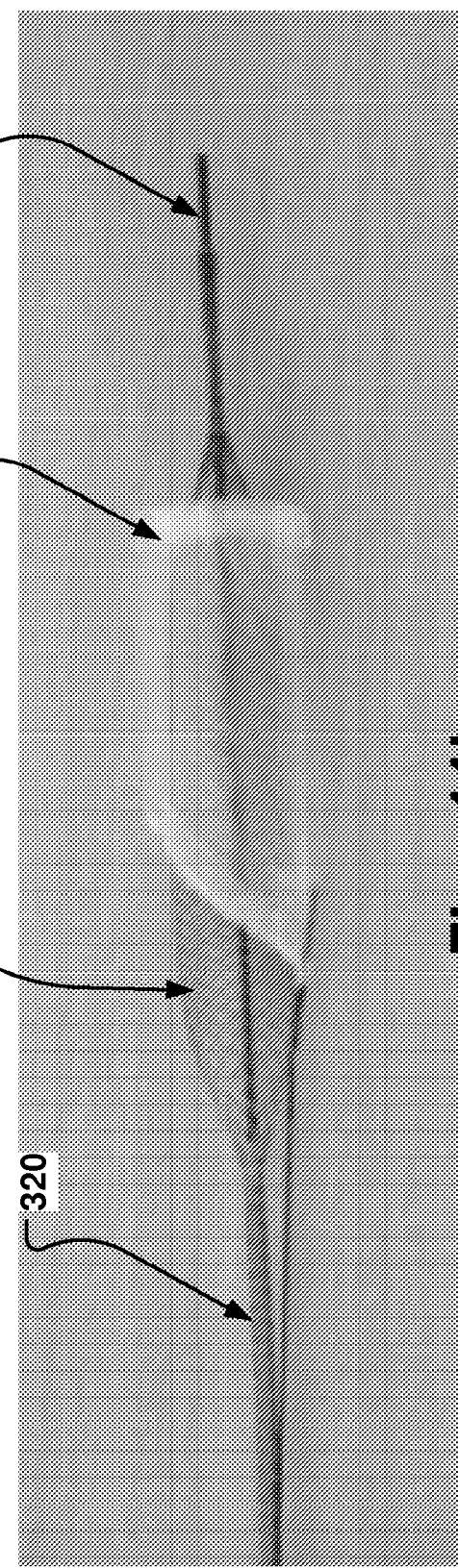
Fig. 11a
Fig. 11b

MEDICAL DEVICE, METHOD AND SYSTEM FOR TEMPORARY OCCLUSION OF AN OPENING IN A LUMEN OF A BODY

RELATED APPLICATIONS

This application is a continuation of U.S. Ser. No. 13/063,926 filed 14 Mar. 2011, entitled Medical Device, Method And System For Temporary Occlusion Of An Opening In A Lumen Of A Body, which is the US National Phase of and claims priority to International Patent Application No. PCT/EP2009/061982, International Filing Date 15 Sep. 2009, entitled Medical Device, Method And System For Temporary Occlusion Of An Opening In A Lumen Of A Body, which claims priority to Swedish Patent Application No. 0850015-9 filed 15 Sep. 2008 entitled Medical Device And System For Temporary Occlusion Of An Opening In A Lumen Of A Body And Method Of Temporary Occluding A Fluid Flow Through Such Opening and to U.S. Provisional Application Ser. No. 61/097,315 filed 16 Sep. 2008 entitled Medical Device And System For Temporary Occlusion Of An Opening In A Lumen Of A Body And Method Of Temporary Occluding A Fluid Flow Through Such Opening, all of which are hereby incorporated herein by reference in their entireties.

FIELD OF THE INVENTION

This invention pertains in general to the field of medical devices, systems and procedures. More particularly the invention relates to temporary occlusion of an opening in a lumen of a body. Such occlusion may block a fluid flow from a body main lumen through an opening thereof, e.g. into a body branch lumen, while maintaining a liquid flow through the main lumen of the body. Even more particularly, the invention relates to a medical device, system, and method facilitating or providing such temporary occlusion. In embodiments the medical system comprises an inflatable balloon.

BACKGROUND OF THE INVENTION

For certain medical procedures it is desired to close off fluid flow through an opening of a body lumen, such as in or into a lumen in a patient's body, during the medical procedure.

For instance for local drug administration, drugs are delivered to an organ via a blood vessel. Then, during a certain time after delivery, it is desired to shut off blood flow to the organ via the blood vessel.

During surgical treatment of certain organs, e.g. during acute surgery, it is desired to controlled shut off blood flow to the area of treatment. Also, during planned surgery, it may be desired to controlled shut off a fluid flow through an opening in a lumen.

Hitherto surgical clamps or clips are used to quench blood supply through vessels. However, this may not be possible during acute surgery. Also, supply vessels are sometimes difficult to reach for the surgeon. Thus, major bleeding may occur. Moreover, the clamping of vessels leads to vascular trauma, which is undesired.

One way of occluding a vessel would be using an inflatable balloon in the vessel itself in order to create a temporary total occlusion of the vessel.

Hitherto, inflatable dilation balloons were used to treat strictures, stenoses, or narrowings in various parts of the human body. Known medical procedures involving inflatable, catheter based and transvascularly deliverable, dilation balloons include percutaneous transluminal angioplasty (PTA) and percutaneous transluminal coronary angioplasty (PTCA), which may be used to reduce arterial build-up such as caused by the accumulation of atherosclerotic plaque. These procedures involve passing an inflatable dilation balloon in a catheter over a guidewire to a stenosis with the aid of a guide catheter. The guidewire extends from a remote incision to the site of the stenosis, and typically across the lesion. The balloon catheter is passed over the guidewire, and ultimately positioned across the lesion.

Once the dilation balloon is positioned appropriately across the lesion, (e.g. under fluoroscopic guidance), the balloon is inflated, which breaks the plaque of the stenosis and causes the arterial cross section to increase. Then the balloon is deflated and withdrawn over the guidewire into the guide catheter, and from the body of the patient. A stent prosthesis may be permanently implanted to provide support for the atherosclerotic artery. When such a device is to be implanted, the balloon catheter carries the prosthesis on its balloon and is deployed at the site of the stenosis. The balloon is inflated to circumferentially expand and thereby implant the prosthesis. Thereafter, the balloon is deflated and the catheter and the guidewire are withdrawn from the patient.

However, known inflatable angioplasty dilation balloons are designed to provide their effect under as short time as possible, in order to avoid ischemia distal to the occlusion. A background is that a total occlusion of a coronal vessel for instance may cause a heart thump or skip and may lead to angina akin to a heart attack because the vessel is completely blocked while the balloon is inflated. Another issue is that, the pressure from the blood flow on the proximal part of a standard dilation balloon may cause it to displace in the vessel. When trying to compensate this, e.g. with higher inflation pressure or larger balloon diameter in relation to the vessel inner diameter, this may cause vascular trauma.

When applied in lumen of the urinal tract, trauma and displacement of occlusion balloons is also an issue.

Inflatable balloons have been developed previously that have a through channel, such that the blood flow through the vessel under treatment is not completely blocked during the procedure. Several patents and patent applications have been published on tubular flow-through balloons for partially occluding a blood vessel. Some examples are US2007/0067010, U.S. Pat. Nos. 6,506,180, 6,007,517 and 4,944,745. However, the prior disclosed inflatable balloons having a through channel are not suitable for use in applications for occluding lateral openings in vessels, such as ostia of side branch vessel occlusion. For instance, these known balloons would not have sufficient stability. Due to the fact that a counter force is lacking, the balloons would be "sucked into" the side branch lumen and not reliably occlude the side branch lumen. Positioning of these known balloons would be uncontrolled at lumen branch sites. Also, these known balloons may easily harm the surrounding tissue due to high inflation pressures resulting in rock-like inflated balloons. This results also in a reduced flexibility of the balloons, which is not advantageous when aiming at sealing a side branch lumen fluid tight. A suspension or attenuation is not provided by inflated balloons that are inflated to be stiff.

Occasionally, the angioplasty balloon fails to deflate, after the relatively short inflation time, which may cause serious injuries or even death to patients due to the blood flow blockage.

Furthermore, such existing balloons may be difficult to maneuver into some lumen, as e.g. side branch vessels, for instance due to small size thereof, and/or anatomy restrictions as e.g. narrow bifurcations from main vessels.

Therefore, existing inflatable dilation balloons are not intended or suitable for long term occlusion of lumina.

Moreover, existing dilation balloons are not intended or suitable for reliable long-term occlusion of vessels, as e.g. during a surgical procedure.

Besides the aforementioned risk of inducing ischemia distal to the occlusion, total occlusion of major blood vessels has other drawbacks. For instance, when occluding peripheral vessels, once blood flow is restored, the release of toxic components, which built up during the occluded phase, into the circulation may cause severe side effects, such as vasodilatation that can be clinically difficult to handle sometimes. In addition, embolic material may be released into a blood vessel, in particular when removing the aforementioned clamps or clips. Embolic particles, which may include thrombus, atheroma and lipids, may become dislodged by surgical or catheter manipulations and enter the bloodstream, embolizing in the brain or other vital organs downstream. Cerebral embolism can lead to neuropsychological deficits, stroke and even death.

U.S. Pat. No. 6,183,492 discloses a catheter that includes an introducer and a flow isolator adapted for disposition in a primary conduit to facilitate flow in the primary conduit while inhibiting flow into intersecting secondary conduits. The flow isolator may include a tubular braiding and a surrounding balloon structure. The flow isolator is released from a catheter and the braiding elastically self-expands to a size smaller than the vessel diameter. Then the device is positioned at the intersection and the balloon is inflated for inhibiting flow into the intersecting secondary conduits. A primary application disclosed is peripheral, hepatic surgery.

However, the devices disclosed in U.S. Pat. No. 6,183,492 are difficult to position in lumen of high flows, e.g. in vessels close to the heart. This is partly due to the fact that the flow isolator disclosed in U.S. Pat. No. 6,183,492 is not suited for applications were a large inner diameter is necessary for a high flow through the primary conduit. Such applications are for instance in vessels close to the heart. When positioning a flow isolator in a vessel close to the outflow of the heart, the cardiac output should be influenced as little as possible. Another issue with the inflatable device disclosed in U.S. Pat. No. 6,183,492 is that it released from a catheter and then positioned in a fluid flow to a vessel intersecting position. In high flow vessels, this would make a reliable sealing of secondary conduits difficult, as the device could not be quickly enough positioned before tumbling and generating turbulent flow in the primary conduit. Also, inflating the balloon in such an environment would make the aforementioned difficulties worse, increase pressure upstream the device, and influence cardiac output substantially.

Thus, there is a need for a novel or improved medical system, device and method of temporary occluding an opening or structural weakening in lumina in a body, or for preventing an undesired fluid flow out of an opening in a lumen over an extended time.

Hence, an improved medical system, device, method, and medical procedure would be advantageous and in particular allowing for increased flexibility, versatility of application including high-flow applications, cost-effectiveness, and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a medical device, a medical system, a kit, and a method of temporary occluding an opening or supporting a weakened wall of a body lumen according to the appended patent claims.

Fluid communication through the opening is temporary prevented, e.g. a fluid flow from a main lumen of a body through an opening in the main lumen at a site inside the body is prevented.

According to a first aspect of the invention, a medical device is provided. The medical device is a medical occlusion device adapted to temporary facilitate or provide occlusion of a fluid flow from a main lumen of a body into an opening in a wall of the main lumen at a site inside said body. The medical device is collapsible and expandable for transluminal delivery to and from the site, and comprises a first inflatable balloon and at least one support structure. The first inflatable balloon has a longitudinal dimension that extends substantially between a proximal end and a distal end of the first inflatable balloon. The first inflatable balloon further has a radially inner wall and a radially outer wall. The radially inner wall and a radially outer wall are arranged at a radial distance from each other when the first balloon is in an inflated state. The first balloon surrounds with its inner wall an inner hollow when in the inflated state. The medical device is thus configured to provide a longitudinal fluid flow passage through the inner hollow. The support structure is at least one collapsible and expandable support structure, which is longitudinally arranged at least partly between the proximal end and distal end of the first balloon, and radially arranged at the inner wall of the first balloon. The support structure, when in an expanded state, is configured to support a patency of the inner hollow of the first balloon in the inflated state thereof. The outer wall of the first balloon is devised for at least partly apposition to an inner wall of the main lumen at the site. The medical device is thus devised to keep a passage of the fluid through the main lumen open, and a passage of the fluid into or through the opening is substantially sealed, blocked, cut off, or obstructed, when the device is deployed at the site.

In embodiments, the support structure may be a wire mesh, net, or similar frame.

According to a second aspect of the invention, a medical system is provided. The medical system is devised for temporary closure of an opening of a main lumen of a body at a site inside the body. The system comprises at least one medical device according to the first aspect of the invention, and a catheter comprising a catheter shaft and a catheter sheath. The aggregate of the medical device is associated with the catheter shaft at a distal end portion thereof, and the catheter sheath is arranged to restrict expansion of the aggregate when positioned in the catheter sheath. Furthermore, in an embodiment, the catheter sheath is retractable from the catheter shaft to allow expansion of the aggregate at the site for the temporary closure. Alternatively, or in addition to the catheter sheath, an expansion unit may be comprised in the system, arranged to provide an active expansion of the support structure.

The catheter shaft may comprise a guidewire lumen for passage of a guidewire to position the catheter within the main vessel at the site, and at least one inflation lumen for inflating at least the first balloon. The guidewire is arranged in the guidewire lumen.

According to a third aspect of the invention, a kit is provided. The kit is a kit comprising at least two of the medical devices according to the first aspect of the invention. The individual medical devices are spaced apart from each other and interconnected to each other by a fluid leakage tight interconnection unit, which is comprised in the kit. The interconnection unit is adapted to provide a through-flow of fluid between inner hollows of first balloons of the individual medical devices.

The interconnection unit may be a tubular interconnection unit having a fluid tight tubular wall between a proximal end and a distal end of the tubular interconnection unit. The proximal end of the tubular wall is connected to a distal opening of the inner hollow of a proximal of the medical devices. The distal end of the tubular wall is connected to a proximal opening of the inner hollow of a distal of the medical devices in order to provide a fluid channel between the inner hollows.

In an embodiment, a proximal of the medical devices of the kit is adapted to be positioned proximally of an opening in a lumen, e.g. proximally of an ostium of a branch lumen into a main lumen. Further, a distal of the medical devices is adapted to be positioned distally of the opening, e.g. the ostium. The tubular wall is non-elastic and flexible and adapted to be arranged along the ostium, in the main lumen and at a distance from the ostium, without contacting tissue of the main lumen, ostium or branch lumen. Arteriosclerotic plaque may often deposit at tissue of ostia at vessel branch sites. Thus, the generation of debris into the side branch vessel upon removal of the occlusion device is advantageously avoided.

A plurality of openings may be occluded by a device or kit as described above.

According to a fourth aspect of the invention, a method is provided. The method is a method of temporary occluding a fluid flow from a main lumen of a body into an opening in the main lumen at a site inside the body. The method comprises transluminally delivering a medical occlusion device in a collapsed state thereof to the site, and expanding the medical occlusion device at the site at least partly by inflating a first inflatable balloon of the medical occlusion device substantially between a proximal end and a distal end thereof, thus appositioning an outer wall of the first balloon at least partly to an inner wall of the main lumen at the site, and keeping open a passage of the fluid in the main lumen through a inner hollow of the first inflatable balloon interior of an inner wall thereof, and thus substantially sealing off a passage of the fluid into or through the opening when the medical occlusion device is deployed at the site, and providing a longitudinal fluid flow through the inner hollow, and after an occlusion time and transluminally retracting the re-collapsed medical occlusion device from the site.

Further, the method may comprise radially expanding a support structure. The expanding is performed in a longitudinal extension of the medical device at least partly between the proximal end and distal end of the first balloon, at an inner wall of the first balloon, thus supporting a patency of the inner hollow by the support structure. The expansion of the support structure is performed actively. Active expansion is either based on intrinsic properties of the support structure itself, or on expansion units.

Active expansion of the support structure itself are based on self-expansion of the structure, e.g. based on elasticity and/or a shape memory effect.

Active expansion provided by an expansion unit may be based on balloon inflation, or expansion caused by other units, e.g. wire based control of a degree of expansion of the support structure. Inflating a second balloon that is at least partly arranged inside the inner hollow and the support structure, will provide an active expansion.

The second balloon is inflated to an outer diameter larger than the inner diameter of the first balloon. A wire manipulated from the proximal end of the catheter used for delivery of the medical device may provide the active expansion, e.g. by a relative movement of the support structure to the catheter sheath while being affixed to the latter in at least one point. Expanding a cage of a wire mesh initiated by a central control wire is an example for such a wire manipulation determining the degree of expansion of the support structure (see FIG. 11b or 12).

This provides for a high flow through the main lumen of the device. Such high flow applications are for instance in vessels close to the heart. Cardiac output is substantially not influenced as a large diameter inner lumen is provided for a flow through the main vessel. The device may be positioned in the aorta, or the arteria pulmonalis while cutting off connection to side vessels, openings or tissue wall weakening, while maintaining a natural high flow and cardiac output in the main lumen.

Moreover, due to the fact that a counter force providing support structure is provided, the balloons are not "sucked into" the side branch lumen and reliably occlude the side branch lumen.

The aggregate of support structure and balloon is not detached from the delivery unit. The aggregate is released from a catheter at the site of the opening. As the aggregate is not released from the delivery unit, the delivery is made under great patient safety, and the deployment and sealing procedure is well controlled. The aggregate is reliably kept in position and not washed away by a radially outwardly applied force, which is further improved by the delivery device that is not detached therefrom.

An active expansion beyond a normal or relaxed or natural diameter of the support unit is provided either by self-expansion or an expansion unit. Thus it is provided a control of a sealing effect of the balloon—at the same time without increasing inflation pressure of the balloon.

A scale provided at the proximal catheter end can make the current expansion of the support structure visible.

This procedure may be done using standard Seldinger technique and fluoroscopy. This makes the system user friendly and increases patient safety as a well established clinical method may be used with some modifications according to the invention.

The device may act as a clot filter when expanded in place.

Further embodiments of the invention are defined in the dependent claims, wherein features for the second and subsequent aspects of the invention are as for the first aspect mutatis mutandis.

The system is intended for usage in many different clinical situations where occlusion of a fluid flow from a main lumen into an opening, e.g. an ostium of a side branch lumen is desired. For instance, occlusion of blood flow into a vessel side branch is desired but where the blood flow still can pass through the main vessel.

In embodiments, the device may also be provided and used as a balloon for aortic valvuloplasty and post stent dilatation of percutaneous aortic valves, eliminating the need for rapid pacing, avoiding its negative consequences.

The system and device may be applied to many other body lumina including for example lumina within the central nervous system, gastrointestinal tract, respiratory tract, urinary tract and the heart/cardiovascular system.

In an embodiment, the system has three basic components; a retractable sheath and/or an expansion unit, a first balloon that has a centrally arranged hollow, and a collapsible/expandable support structure at the hollow. The first balloon is for instance mounted/molded onto the exterior surface of the support structure. The aggregate of support structure and the first balloon is positioned and once the sheet has been retracted from the first balloon, the first balloon can be inflated. The support structure may be self-expandable or expandable by an expansion unit, such as a further balloon arranged at its inside. In an embodiment, the lumen of the support structure is chosen to be smaller than that of the vessel lumen. In an embodiment, the outside diameter of the inflated first balloon is chosen to be larger than the interior diameter of the main vessel lumen.

The method may be applied in the field of cancer treatment. For instance, cytostatics drugs are delivered to a tumor infested organ. Then, during a certain time after drug delivery, it is desired to shut off blood flow to the organ via the blood vessel in order to let the cytostatica become effective and not being washed out prematurely. This is made by applying the medical device of embodiments described herein for occluding an opening of a branch vessel leading to the organ under cytostatica treatment.

The method may be applied during surgical treatment of certain organs, e.g. during acute surgery. Here, it is desired to controlled shut off blood flow to the area of treatment. Also, during planned surgery, it may be desired to controlled shut off a fluid flow through an opening in a body lumen.

Other circumstances where it is desired to temporary close off communication through a body lumen by the above method are as follows. It may be desired to close off the opening of an aneurysm or weakened tubular wall from the main lumen. This may comprise protecting the lumen wall at or in the vicinity of the opening or weakening from a fluid pressure in the main lumen until the weakening is treated or the opening closed, for instance by surgical procedures or application of medical repair devices.

The devices are applicable where a damage in a vessel wall is present. Other applications are organs that have branch lumen or vessels.

Medical devices of embodiments described herein facilitate or provide this temporary occlusion in such indications or procedures.

Some embodiments of the invention provide for blood flow through a main lumen while blood flow into a side branch lumen is effectively occluded.

Embodiments provide for atraumatic sealing of an opening in a body lumen.

A graft may be delivered over the outer balloon to repair a damage or weakening in embodiments.

The medical device is in embodiments intended for usage mainly in vascular surgery in operating rooms with access to fluoroscopy imaging facilities (hybrid OR). The medical device may be used in both acute and elective surgery.

The term "occlude" in the present context should be interpreted in a broad sense and means to block or stop up communication, e.g. a passage of flow. It may comprise direct obstruction of an opening as well as indirect closure of fluid flow to, into, via, through and past an opening. Openings are in particular openings in body lumen walls, such as lateral openings, ostia, aneurysm openings, etc.

The term "diameter" should not be construed as merely comprising dimensions of circular cross sections of units, but may also encompass other dimensions of different shapes of the units, e.g. oval, substantially flat, rectangular, etc. The shape may be chosen in dependence of the desired application of the device, system or kit, the particular anatomical site of application, the access way to that site, etc.

The term "support" in the present context should be interpreted in a broad sense and means a source of structural strength, holding up, carrying, reinforcing, sustaining, or bearing.

The term "opening" in the present context should be interpreted in a broad sense and means not only a physically open through structure, like a branch vessel, but also ruptures or other structurally weakened tissue walls of body lumen which will potentially open when not protected, such as present at aneurysms.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 11a is a side view of an embodiment of a medical occlusion device;

FIG. 11b is a side view of an embodiment of a medical occlusion device;

DESCRIPTION OF EMBODIMENTS

Figure 1:
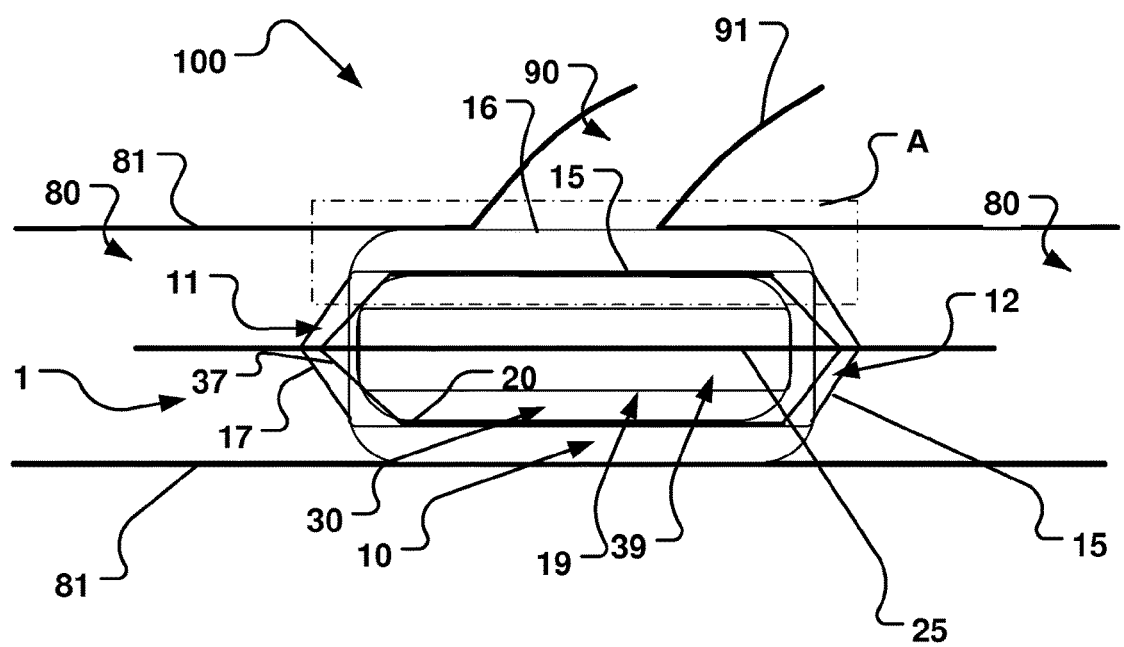
FIG. 1 is a schematic drawing illustrating a medical occlusion device when positioned at a branch lumen.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable to body lumen in form of blood vessels and in particular to a side branch blood vessel branching from a main blood vessel, or other openings in blood vessels, e.g. ruptures, or openings into aneurysms. However, it will be appreciated that the invention is not limited to this application but may be applied to many other body lumina including for example lumina within the central nervous system, gastrointestinal tract, respiratory tract, urinary tract and the heart/cardiovascular system. In addition, weakened lumen walls, such as aorta aneurysm in an early stage before rupturing, are another field of application of medical devices of the invention.

In an embodiment of the invention according to FIG. 1, a medical device 1 is shown. The medical device is adapted to temporary occlude a fluid flow from a main lumen 80 of a body into a branch lumen 90 at a branch site 100 inside the body, or to close another type of opening or weakening 85 in a tissue wall 81 surrounding the lumen. Main lumen 80 has a tissue wall 81 and branch lumen 90 has a tissue wall 91. The opening 85 of the branch lumen 90 into the main lumen 80 is also called ostium. The body is a human or animal body, e.g. a body of a mammal.

The medical device is collapsible and expandable for transluminal delivery to and from the branch site 100. In FIG. 1 the device 1 is shown in its expanded state, deployed and released put of a delivery catheter, and positioned at a branch lumen 90 and preventing a fluid flow from the main 80 into the side branch lumen 90. However, the device 1 remains affixed to the delivery unit via a wire 45. That means the side branch lumen 90 is fluidly disconnected from the main lumen 80. Communication or a flow of fluid through the ostium into the side branch lumen is blocked. This is done in an effective way. Positioning is made in accordance with medical procedures to which the medical practitioner is well acquainted, which will be described further below.

The medical device 1 comprises an aggregate of a first inflatable balloon 10 and a support structure 20. The first inflatable balloon 20 has a longitudinal dimension that extends substantially between a proximal end portion 11 and a distal end portion 12 thereof. The first balloon 1 comprises a radially arranged inner wall 15 and a radially outer wall 16 at a radial distance therebetween when the first balloon 1 is in an inflated state, as shown in FIG. 1. In the collapsed state, or when the balloon 10 is not inflated, also the outer wall 16 may be adjacent the support structure, besides inner wall 15. When the first balloon is in the inflated state, the inner wall 15 surrounds or encircles an inner hollow 19 configured to provide a longitudinal fluid flow passage through the inner hollow 19, see for instance the arrows illustration such a flow in FIG. 4. The first balloon 10 may be inflated via one or more inflation lumen 17.

The aggregate comprises at least one support structure 20. In FIG. 1 the support structure 20 is illustrated as a tubular member. Embodiments of the medical device comprise at least one collapsible and expandable support structure 20, longitudinally arranged at least partly between the proximal end 11 and distal end 12 of the first balloon 10, and radially arranged at the inner wall 15 thereof. The support structure 20 may also extend beyond the ends 11, 12 of the balloon, see e.g. FIG. 11b. The support structure 20, when in an expanded state, supports a patency of the inner hollow 19 of the first balloon 10 in the inflated state thereof.

Thus several advantages are achieved. The first balloon 10 is substantially kept in a desired substantially toroid or doughnut shape, independent of the anatomical surrounding situation. Furthermore, the passage through the aggregate, allowing fluid flow through the first balloon 10 at the branch site 100, is reliably upheld. Movements of the body at the branch site 100, e.g. by vessel contractions or pulsatile flows of fluid in the main lumen 80, do substantially not influence the sealing effect of the aggregate, maintaining the cut-off communication at the opening of the branch vessel.

The support structure 20 also provides a counter force to the elasticity of a wall 81 of a lumen in which the aggregate is positioned and inflated. In addition, a counter force to an inward movement of the inner balloon wall 15 is provided by the support structure, maintaining the lumen open to a large extent, which allows for a low profile of the balloon 10 cushion in relation to the entire diameter of the body lumen. Thus a more reliable fixed positioning in the lumen is provided as the balloon is pressed between the vessel, acting inwards, and the support structure, and acting as counter point and/or outwards.

In addition the sealing at the tissue wall is effectively improved by this force provided by the support structure 20. Moreover, the tissue of the lumen wall is treated gently and not injured. The cushion effect of the inflated balloon 10, having an inherent flexibility of its gently inflated toroid lumen, allows for an advantageous appositioning of the lumen wall.

Inflation pressures of the first balloon are chosen, such that the balloon is inflated such that the suspension effect of the inflated balloon between the support structure and the lumen wall is provided. The first balloon 10 is not inflated to such an extent as to expand the lumen wall such that damages occur in this wall. Inflation pressure is provided such that a reliable sealing is provided, which might be verified in real-time, e.g. by fluoroscopy and suitable contrast agents. This inflation pressure is magnitudes lower than that needed for conventional angioplasty balloons. Still, the device is reliably kept in position and not washed away. A certain degree of expansion of the tissue wall 81 by the expanded aggregate may be allowed.

The outer wall 16 of the first balloon is devised for at least partly apposition to an inner wall of the main lumen 80 at the branch site 100. As shown in FIG. 1, the outer wall is in apposition to the lumen wall proximally and distally of the ostium 85.

Figure 5:
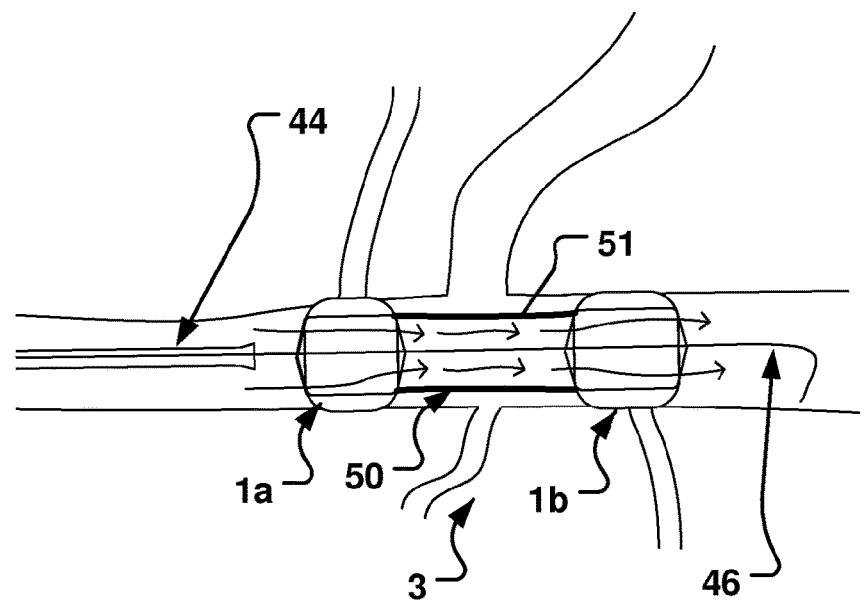
FIG. 5 is a schematic illustration of a kit of medical occlusion devices when stopping fluid flow into a side branch lumen.

In other embodiments, as e.g. shown in FIG. 5, the entire outer wall, or at least a radially outer portion thereof, may be in apposition to the main lumen 80 inner tissue wall surface. The radially outer portion may be substantially straight in longitudinal extension of the balloon 10.

In this manner a fluid passage through the main lumen 80 is kept open and a communication through the opening, e.g. as a passage of fluid, into the branch lumen 90 is substantially sealed when the device 1 is deployed and expanded and inflated at the branch site 100. At the same time, the device 1 is anchored reliable at the branch site in the main lumen 80 against the wall of the lumen and by remaining affixed to the delivery system, e.g. a delivery wire, catheter, etc.

When the device is given a suitable longitudinal dimension, it may cover a plurality of openings and thus occlude flow into these openings. This may be advantageous, if several openings are positioned at different radial and longitudinal positions of the lumen. Also, in case the lumen wall is sensitive, e.g. there is a risk of lumen wall rupture, a lumen wall weakening, or a plurality of smaller openings, these conditions are advantageously sealed off by embodiments of the invention, including devices having long longitudinal extensions, or other embodiments, as e.g. shown and described with reference to FIG. 5. The balloon has a longer longitudinal extension than the opening or weakening of the tissue wall 81.

The inner wall 15 and outer wall 16 are coaxially arranged in relation to each other and the inner hollow 19 is centrally arranged within the inner wall 15 and within the support structure 19, when expanded. Further, the support structure 20 is a tubular support structure comprising a generally cylindrical body arranged at an inner wall boundary of the first balloon 10 to the hollow center 19. The support structure 20 is positioned coaxially with the first balloon 10 in the hollow center 19 at the inner boundary of the first balloon 10.

Figure 4:
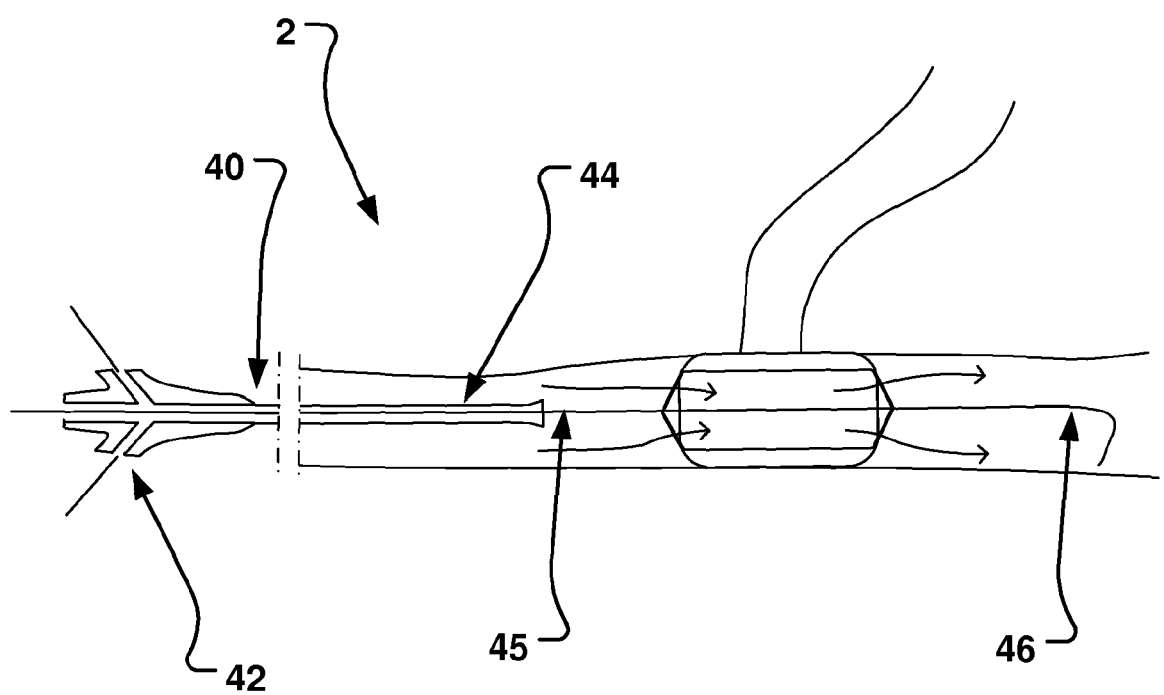
FIG. 4 is a schematic illustration of a medical system during occlusion of a side branch vessel.

The support structure 20 may be self expandable. In these embodiments, the support structure is restricted to expand during delivery to the branch site or opening, e.g. by means of a catheter sheath 44 (FIG. 4). When the aggregate is released from the restriction, e.g. by retracting sheath 44, the self expandable support structure 20 radially expands, together with the first balloon 10 getting inflated, whereby the first balloon is expanded, and the aggregate is positioned at the opening 85, as e.g. shown in FIG. 1.

The self expanded, relaxed or natural diameter of the support structure 20 is larger than the diameter of the inner wall 15 of the balloon in its relaxed or natural diameter when inflated with the necessary inflation pressure to obtain a reliable sealing of the opening 85. The self expanded, relaxed or natural diameter of the support structure 20 may even be larger than the outer wall 16 diameter or the natural diameter of lumen 80. In this manner, a outwardly oriented force 151 is permanently present during the temporary sealing of the opening 85.

Figure 10A:
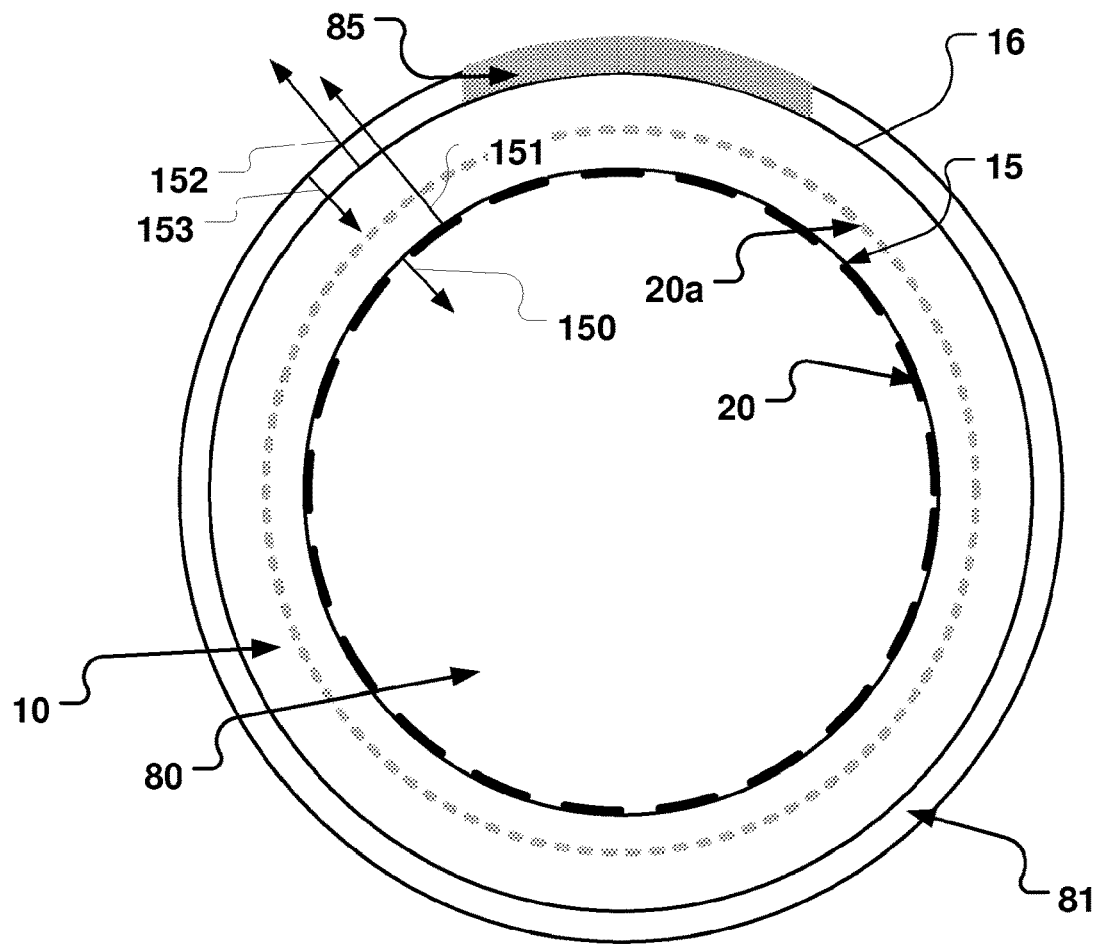
FIG. 10a is a cross sectional view through a medical occlusion device at an opening in a body lumen.

The expanded state of the aggregate is shown in cross section in FIG. 10a.

The support structure 20 may be affixed to the inner wall 15 by suitable fixation units, such as glue, threads, anchoring elements, etc. The support structure may also be provided separate from the first balloon 10 and releasably affixed to the first balloon 10 inner wall by an active radially outwardly oriented expansion force in the released state.

In other embodiments, the support structure 20 is not self expandable and needs to be expanded by an expansion unit to an expanded state 20a, e.g. by means of a delivery unit. The support structure 20 is for instance balloon expandable and/or expandable by other active expansion units.

Figure 2:
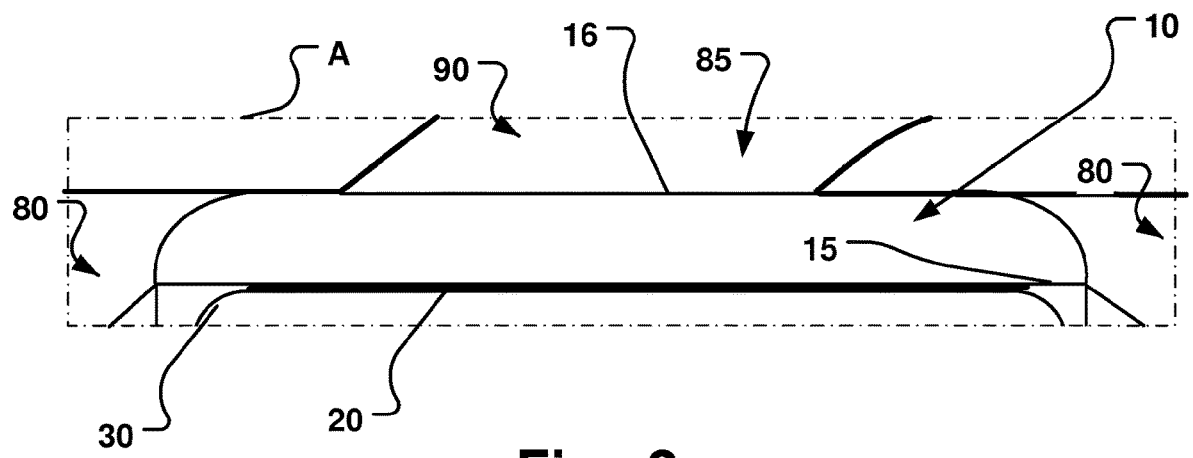
FIG. 2 is a schematic drawing showing an enlarged portion of FIG. 1.

For this purpose, for instance a second balloon 30 is provided that is adapted to expand the tubular support structure 20, and is at least partly arranged inside the inner hollow 19 of the first balloon 10. The second balloon 30 is longitudinally at least extending between the proximal end and distal end of the support structure 20, such that the entire support structure 20 is expanded upon inflation of the second balloon 30, see FIG. 2.

The second balloon 30 may be deflated and retracted upon expansion of the support structure 20. Alternatively, or in addition, the second balloon 30 may also have an inner hollow 39. The inner hollow 39 allows for a fluid flow therethrough when the second balloon is inflated. In this manner, the second balloon 30 may be left in place during a time of occlusion of the branch lumen 90. Also, during inflation, the main fluid flow is not entirely reduced.

For inflation of the balloons, inflation lumina are provided. A first inflation lumen 17 is associated with the first balloon 10 and a second inflation lumen 37 is associated with the second balloon 30.

Figure 3:
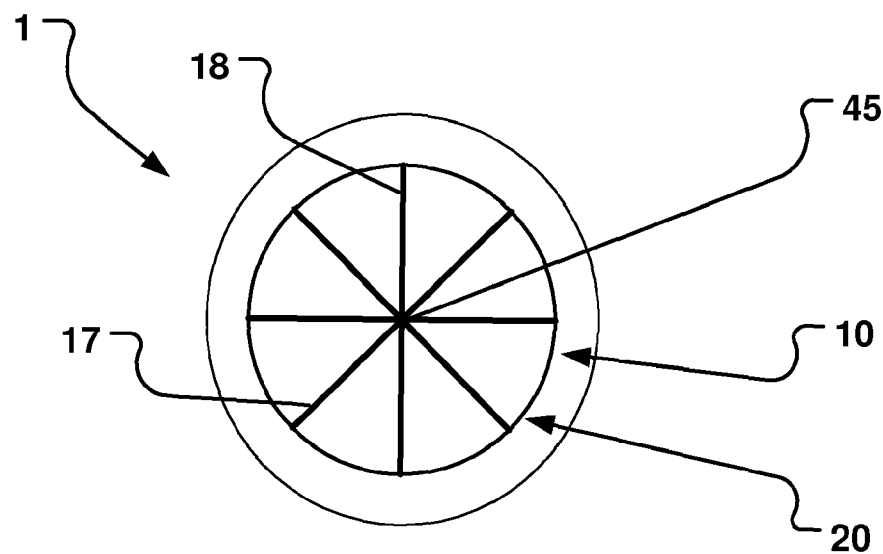
FIG. 3 is a cross sectional view in longitudinal direction of a medical occlusion device.
Figure 12:
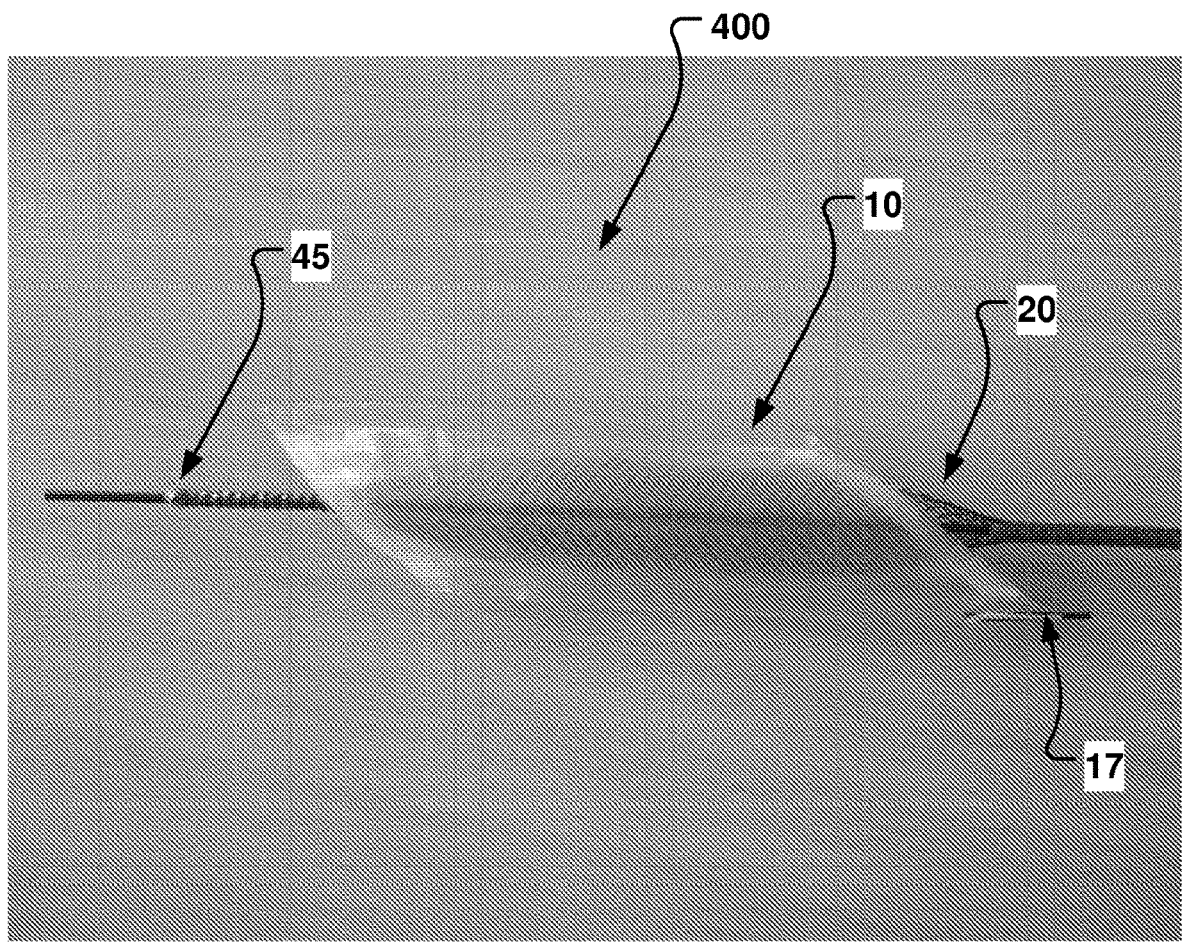
FIG. 12 is a side view of an embodiment of a medical occlusion device.

FIG. 3 is a cross sectional view in longitudinal direction of the medical occlusion device 1 showing the inflation lumen 17 extending from a catheter shaft 45. Support webs 18 are provided for attaching the support structure 20 to the catheter shaft 45, or central delivery wire, and/or an active expansion unit. The support webs may be arranged as leading support webs 18. The support webs 18 may be integral with the support structure 20, such as integral with a mesh, optionally extending longitudinally beyond the balloon 10, as shown in FIG. 11b or 12. In addition, further support webs may be provided inside the inner hollow 19, and at the trailing end of the medical device 1. Leading support webs 18 facilitate collapsing the medical device 1 and re-inserting it into the sheath 44 for withdrawing the medical device from the branch site 100 and out of the body. The webs may constitute a filter unit for the fluid flow through the main lumen 80 when the aggregate is in place at the opening 85. The filter unit may be a blood clot filter. A degree of filtering may be determined by the pick and pitch of a braiding, or a radial and/or longitudinal number of webs, of the support structure 20.

Trailing webs facilitate insertion of the aggregate into a catheter, which is automatically collapsed when pushed into a proximal opening of the catheter lumen.

The first and second inflation lumina 17, 37 may be arranged to be in fluid communication with each other. In these embodiments, simultaneous inflation of both the first and second balloon is provided. This may provide an easy installation of the medical device 1 at the branch site 100. The medical practitioner only needs to take care of a single inflation step, whereupon the medical device is securely positioned.

In another embodiment the first and second inflation lumina 17, 37 are not in fluid communication with each other. Individual inflation of the first and second balloon is provided. This embodiment may be preferred in certain anatomical situations, where e.g. an initial positioning of the device is made by inflating the first balloon 10, when the support structure is not self expanding. Subsequently, the second balloon 30 is inflated to expand the support structure 20, and to thus securely anchor the medical device 1 and to provide a support for the inner hollow 19 for fluid communication, as well as sealing of the opening 85. Further, the second balloon 30 may then be withdrawn, which leaves a large diameter open lumen through the aggregate for fluid flow. This is in particular of interest for high-flow applications, e.g. close to the heart output in order to maintain cardiac output.

Thanks to the coaxial arrangement of the first balloon 10 and the second balloon 30 in the hollow inner 19 of the first balloon 10, even the second balloon's inner hollow 39 provides a longitudinal through-passage through the medical device 1 when positioned at the branch site 100.

The second balloon 30 may be arranged to be deflated and retracted upon expanding the support structure 20. In this manner, the diameter of the through-passage substantially corresponds to the diameter of the inner hollow 19, as the support structure is substantially flat compared to the radial extension of the inner hollow 19. Thus, the through-flow capacity of the through passage is enhanced in comparison to having the second balloon 30 arranged therein and determining the diameter of the through passage by its inner hollow 39.

The second balloon 30 may have a section with larger diameter in at least one end portion thereof for expanding the support structure in sections with different diameters.

In some embodiments, the support structure 20 is at least partly attached to the inner wall 15 of the first balloon 10 on an outside wall surface of inner wall 15 at the inner hollow 19 side.

The support structure 20 may alternatively, or in addition be integral with the inner wall 15 of the first balloon 10. The support structure 20 may in particular be molded together with the inner wall 15.

Alternatively, the support structure 20 is attached to the inner wall 15 of the first balloon 10 on an inside wall surface thereof, inside the first balloon. Thus, improved fluid flow in the inner hollow may be provided.

The support structure 20 will, when expanded, the common radial position when in an equilibrium with the counter acting inflation force of inner wall 15 upon inflation of the first balloon 10.

In case the support structure 20 is actively expanded from its collapsed configuration to its expanded configuration by an expansion unit, the retractable sheath may be omitted. A restriction of the support structure 20 in its collapsed configuration is not necessary.

For instance, the expansion unit may comprise a pusher or pushing sheath that is arranged to suitably actively expand the non-self-expandable support structure 20. The expansion unit may comprise arms or a resiliently expandable structure that pushes the support structure 20 from its interior outwardly to an expanded, open configuration, where it supports the first balloon and provides the actions and functions described herein.

The expansion unit may be the second balloon 30 described above.

In addition the first balloon 10 may support the expansion of the support structure 20 during it is being inflated.

The first balloon 10 may be inflated before, after or during expansion of the support structure 20, upon release from the delivery catheter at site 100.

The first balloon has a maximum inflation pressure, as will be explained below with reference to FIG. 10a. The maximum inflation pressure is suitably below a burst pressure of the balloon 10. The first balloon 10 is inflated to a pressure less than this maximum inflation pressure, at least during positioning at the body site and/or during the entire occlusion/sealing phase. Thus, the first balloon 10 may be especially tissue friendly positioned in the lumen. A partly inflated first balloon 10 provides in particular a soft cushion effect for special soft apposition to wall tissue of the lumen in which it is expanded.

The first balloon 10 may be partly or not at all inflated during expansion of the support structure. It may be folded, bend or doubled for a compact delivery arrangement. The first balloon 10 is for instance not inflated during expansion of the support structure 20. In this manner the support structure 20 is expanded to a diameter substantially equal to the inner diameter of the lumen 81. Inflation of the first balloon upon expansion of the support structure thus ensures that the first balloon is expanded to a larger diameter than the inner diameter of the lumen 81. The inflation degree of first balloon in relation to the maximum inflation pressure provides a selectable degree of tissue anchoring of the medical device at the body site.

In embodiments the expanded support structure 20 is configured to bear against the force of the first balloon directed inwardly when inflated. Thus the outward expansion of the first balloon is ensured while preventing that the balloon is sucked into the opening 85. A certain degree of radial flexibility to a smaller diameter may occur in equilibrium, see FIG. 10a.

When expanded, the support structure 20 may be releasably locked in its expanded configuration during the time of occlusion. This may for instance be provided by a snap or click mechanism. Bistability of the support structure between two points of minimum energy (collapsed and expanded) may be provided alternatively, or in addition to the locking functionality.

The support structure 20 may be a tubular structure that comprises a mesh of wires. Alternatively, or in addition, it comprises a pattern of struts and connectors, such as a zigzag pattern, as known from stent technology.

A stent includes a cylindrical frame consisting of a series of helical winds containing a pattern of alternating zigzag bends. The frame may be made of resilient wire or from a piece of laser cut hypo tubing.

For instance, in U.S. Pat. No. 6,572,647 a method of making such a stent is disclosed, which is incorporated herein by reference in its entirety. The laser cut stent for transluminal delivery has windows in its cylindrical wall, the windows giving the stent enhanced flexibility during delivery along said lumen. The method of making such a stent involves removing from the wall of a tube enough material to leave the tube wall penetrated in a multiplicity of separate cut lines, in a pattern which permits the tube to expand. The tube is then expanded and then a plurality of tube wall scrap portions are removed from the tube wall between adjacent cut lines, thereby to introduce a plurality of spacings between adjacent stenting zones of the tube wall surface, these remaining after compression of the tube to a configuration to allow it to be advanced along a tortuous bodily lumen. Advantageously, the material of the tube is a shape memory alloy and the tube is for a self-expanding stent.

However, stents were hitherto always positioned on the outside of an inflatable balloon for expansion and permanent implantation. Stents are devised for apposition to vessel tissue. In contrast, the present support structure 20 is devised for apposition to an inner balloon wall, supporting the balloon, and having a toroid balloon sealing cushion between the support structure 20 and the lumen inner wall tissue.

Alternatively, or in addition to a tubular structure, the support structure may comprise a plurality of radial support webs 18 in addition or alternatively to the tubular structure disclosed herein. The webs 18 are arranged from a catheter shaft 45 or a delivery wire. Webs 18 may for instance be pre-tensioned to provide a radially outwardly directed force supporting the first balloon at the branch site 100.

A length of the support structure 20 and a length of the second balloon 30, if arranged therein, is in an embodiment larger than a length of the longitudinal dimension of the first balloon 10. This is illustrated in FIGS. 6 and 11b, where longitudinal extensions 21, 22 of the support structure 20 are shown.

Figure 6:
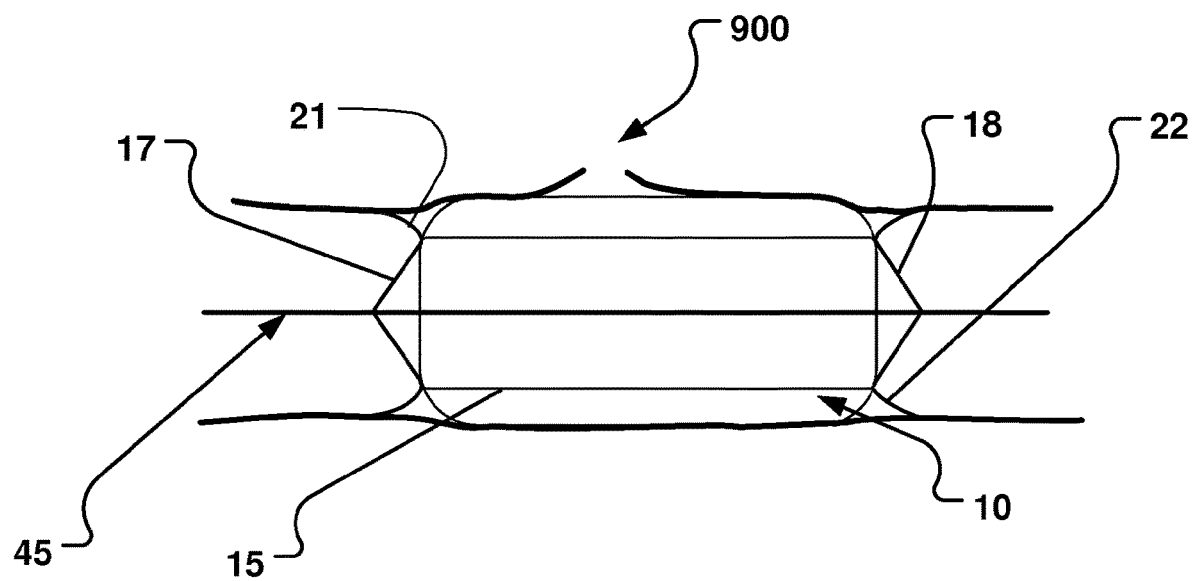
FIG. 6 is a schematic illustration of another medical occlusion device positioned at an abnormal lumen opening.

The first balloon 10 shown in FIG. 6 is positioned at an abnormal lumen opening 900. The abnormal lumen opening may for instance be a rupture, hole, damage, aperture or other opening. The abnormal opening necessitates a medical measure, e.g. a surgical repair or installation of a graft. The device 200 provides temporary occlusion of a fluid flow out of the main lumen through the abnormal opening. During the temporary occlusion time, a medical procedure may be performed in order to remedy the abnormal opening. Upon completion of the medical procedure, the abnormal opening is closed and a leak of fluid through the wall of the main lumen will no longer occur. The temporary occlusion device 200 is then removed from the temporary occlusion site.

Figure 8:
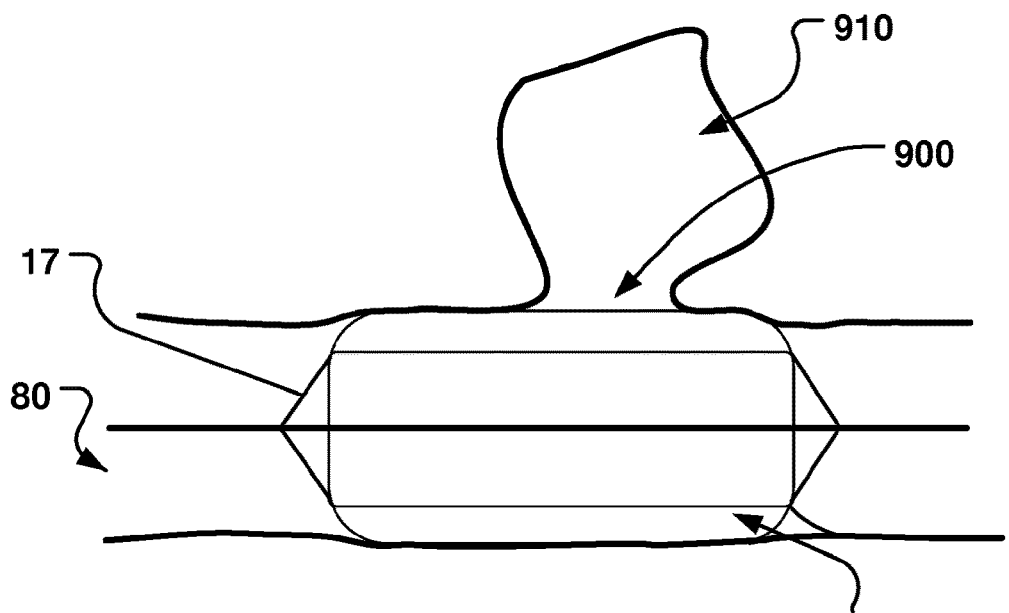
FIG. 8 is a schematic illustration of another medical occlusion device positioned at an aneurysm of the main lumen.

Another example is the occlusion of an aneurysm 910, as illustrated in FIG. 8. A fluid communication or flow from the main lumen into the aneurysm is stopped, in a similar manner as described above with reference to FIG. 6. Here, a rupture of the aneurysm has not yet occurred and the vessel wall is intact but weakened. A pressure relief is provided by the temporary communication cut off of occlusion device 200.

The opening or abnormal opening in the context of the present application is usually a lateral opening in the wall of the lumen.

Returning to FIG. 6, it can be seen that the proximal end and/or the distal end of the support structure 20 is constructed such that it is expandable to a greater outer diameter than an inner diameter of the inner hollow 19 of the first balloon 10.

The extensions 21, 22 at the proximal end and/or distal end of the support structure 20 may be outwardly flared towards the outer wall of the first balloon 10 and oriented away from the proximal end and/or distal end of the first balloon 10, respectively. In this manner, a fluid guide is provided that advantageously minimizes turbulences of fluid flow in the main lumen 80 through the medical device 1. Further, sealing is improved.

Thus, the medical device 1 is provided with a support structure 20 that comprises at least a proximal extension 21 extending proximally longitudinally beyond the proximal end 11 of the first balloon 10. The proximal extension 21 may comprise a cover or fluid tight layer or coating for tissue friendly contacting an inner tissue wall of the main lumen 80 proximally the first balloon 10. Thus, a fluid guide into the inner hollow 19 of the first balloon 10 is provided upon expansion of the support structure 20 and its proximal extension 21.

The support structure 20 comprises in embodiments a distal extension 22 extending distally longitudinally beyond the distal end of the first balloon. The distal extension may comprise a cover or fluid tight layer or coating for tissue friendly contacting an inner tissue wall of the main lumen 80 distally the first balloon 10, such that a fluid guide out of and/or into the inner hollow of the first balloon is provided upon expansion of the support structure 20 and its distal extension 22.

One or more of the extensions 21, 22 may be provided as a sealing flange. The sealing flange may be made of a suitable fabric.

The longitudinal extensions of the support structure 20 may have a heat set shape to an extension of an outer diameter of the first balloon. The longitudinal extension of the support structure is at least as large as the diameter of the opening 85. In this manner, the fluid guide and tissue apposition of the extension to the main lumen inner wall provide a particularly advantageous fluid tight sealing and cut off communication over the opening. Occlusion of a fluid flow into side branch lumen 90 is effectively provided.

In the embodiment, the first balloon has a balloon body of elongate torus shape, when inflated.

The outer wall 15 of the first balloon 10 is at least partly devised for soft tissue apposition to the inner wall of the main lumen 80 at a first portion of the outer wall, such that the device is configured to securely and sealingly engage the main lumen. The outer wall is preferably thin walled, providing a tissue friendly apposition to the tissue wall.

The outer wall 16 and the inner wall 15 of the first balloon 10 may have sections of different rigidity. The different rigidity is for instance provided by different wall thicknesses of the sections of the outer wall and the inner wall. The outer wall 16 of the first balloon 10 has e.g. proximal and distal end portions that have a wall thickness that is larger than a wall thickness at the central elongate portion of the outer wall 16. Thicker portions may advantageously be oriented towards the opening in the delivered state. In this manner, patency of the longitudinal channel of the medical device 1 through the main lumen 80 is reliably closed off, providing an occlusion of the side branch vessel 90.

A ratio of a maximum outer diameter of the first balloon 10 in relation to maintained passage lumen diameter of the inner hollow 19 is in the range of 40% to 90%. The ratio may be 75% to 90%, such as 80%, 85% or 90%. Such high ratios are possible thanks to the natural expanded diameter of the support structure 20 being larger than the natural inflated inner diameter of the balloon 10.

The medical device 1 may comprise radiopaque markers. Alternatively, or in addition, the first balloon 10 is adapted to be inflated with radiopaque material. This facilitates positioning of the medical device 1 at the branch site 100 under fluoroscopy.

The lumina are in specific embodiments blood vessels. The outer wall 15 is configured to be arranged to sealingly cover an ostium of the branch lumen 90 at the branch site 100.

The first balloon 10 is adapted to be inflated over an extended period of time for occluding the ostium to the side branch lumen, e.g. during a surgery of an organ supplied with blood by the side branch vessel 90.

The aggregate of a first balloon 10 and inner support structure 20 is re-collapsible after expansion, such that the device is transluminally removable from the branch site and out of the body upon a time of occlusion of the branch lumen 90.

As shown in FIG. 6, the outer diameter of the first balloon 10 may be chosen slightly larger than the inner diameter of the main lumen 80. In this manner a reliable positioning of the medical device 1 in the main lumen 80 is provided, while not harming any tissue thereof.

FIG. 10a is a cross sectional view through a medical occlusion device at an occlusion site in a body lumen. Various forces acting in the expanded state of the aggregate when positioned at an opening 85 are illustrated by arrows 150-153.

A first force acts radially inwards and is caused by the pressurized inner wall 15 of the balloon 10. A second force 151 caused by the expansion force of the support structure 20 counteracts this first force 150. The support structure is not fully expanded.

In case the support structure 20 is self expandible, the outer diameter of the structure 20 at its relaxed state is larger than the inner diameter of the balloon 10 at inner wall 15 when inflated and without an acting counter force.

When the support structure is not self expandable, this state can be provided in various ways. For instance, a wire cage may be actively expanded, an inner balloon having a passageway of its own may be inflated inside the lumen 80, webs may resiliently push the inner wall 15 radially outwards, etc.

The dotted line 20a illustrates a possible position of the structure 20 when fully expanded without counter force.

The outwardly oriented expansion force 151 of the support structure 20 is larger than the inwardly oriented inflation force 150. Thus the support structure will be tensioned against the wall 15 and may not be affixed to the latter, allowing for a relative movement of the two latter relative each other, whereby deployment, expansion, and retrieval is facilitated due to reduced forces.

The lumen wall 81 resiliently pushes with a force 153 against the radially outwardly anchoring force 152 of the outer wall 16 of the inflated balloon 15. Anchoring force 152 of the inflated balloon 10 is larger than the lumen force 152. Preferably, the outward inflation force 152 is only slightly larger than inward tissue force 153. Once sealing is accomplished, and thanks to the fact of a large opening close to the natural opening of lumen 80, the fluid flow in the main lumen will be very little influenced. A pressure drop across the aggregate is kept minimal. Therefore, very low inflation pressures will be sufficient for ensuring a reliable sealing of the opening 85

The medical device 1 may be comprised in a medical system 2 devised for temporary closure of a branch lumen 90 of a main lumen 80 of a body into the branch lumen 90 at a branch site 100 inside the body. The system 2 comprises, as illustrated in FIGS. 4, 5 and 11a, at least one medical device 1 a catheter 40 comprising a catheter shaft 45 and a catheter sheath 44. The aggregate of the medical device 1 is associated with the catheter shaft 45 at a distal end portion thereof. The catheter sheath 44 is arranged to restrict expansion of the aggregate when positioned in the catheter sheath 44. The catheter sheath 44 is retractable from the catheter shaft 45 to allow expansion of the aggregate at the branch site 100 for the temporary closure of the side branch vessel.

The catheter shaft 45 comprises a guidewire lumen for passage of a guidewire 46 to position the catheter 40 within the main vessel 80 at the branch site 100, and at least one inflation lumen for inflating at least the first balloon 10. The system 2 furthermore comprises the guidewire 46 arranged in the guidewire lumen of the catheter shaft 45.

Materials for making the balloons can be polyvinylchloride (PVe), cross-linked polyethylene (PE), polyester (PET), polyethylene terephthalate, Nylon, and others. In particular polytetrafluoroethylene PTFE, commercially available as Goretex®, is suitable as a balloon material.

The medical device is in embodiments intended for usage mainly in vascular surgery in operating rooms with access to fluoroscopy imaging facilities (hybrid OR). The medical device may be used in both acute and elective surgery.

During surgical treatment of certain organs, e.g. during acute surgery, it is desired to controlled shut off blood flow to the area of treatment. Also, during planned surgery, it may be desired to controlled shut off a fluid flow through an opening in a lumen as part of the surgical procedure. For instance, in a passive peripheral vessel intervention the medical device may be positioned in the peripheral vessel as an initial step of the intervention.

The device is thus, amongst others, useful for passive interventions, which do not need acute measures.

Figure 9A:
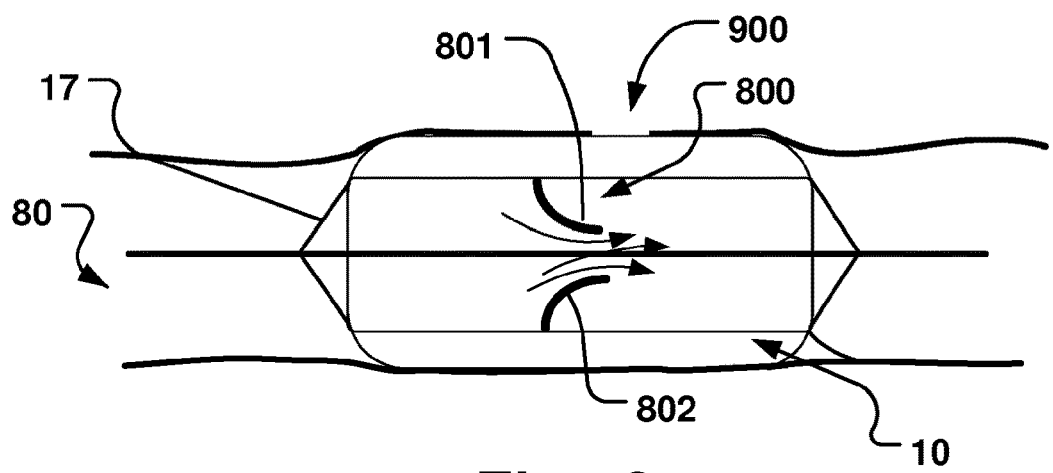
FIG. 9a is a schematic illustration of another medical occlusion device having a unidirectional flow direction unit in an inner hollow thereof.
Figure 9B:
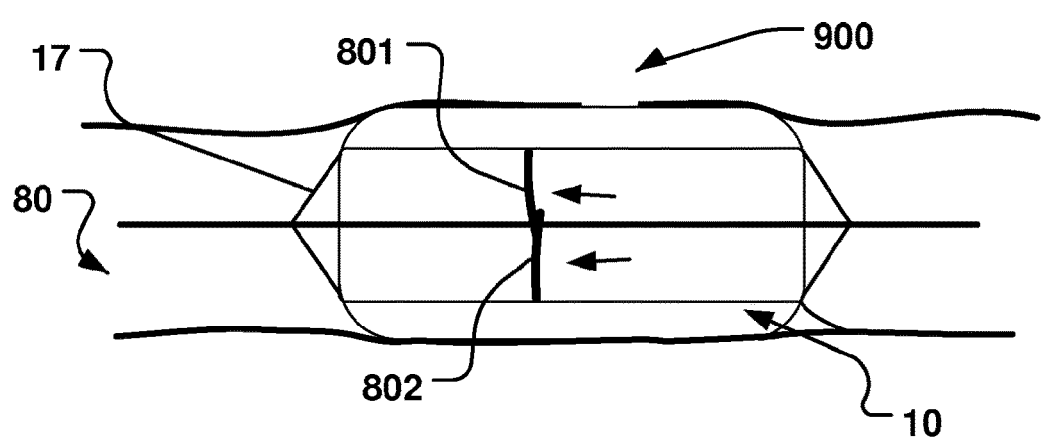
FIG. 9b is a schematic illustration of another medical occlusion device having a unidirectional flow direction unit in an inner hollow thereof.

FIGS. 9a and 9b are schematic illustrations of a medical occlusion device of the type described above having a unidirectional flow direction unit 800 in an inner hollow thereof. By means of the unidirectional flow direction unit 800, the medical device is provided with check valve functionality.

In the embodiment illustrated in FIG. 9, a plurality of valve flaps 801, 802 provide the check valve function. In other embodiments, the unidirectional flow direction unit 800 may comprise a single valve flap, e.g. a circular valve flap having a central fixation at the guidewire or catheter shaft 45.

The valve seat may be provided in a separate structure. For instance the valve seat my be provided as a annular ring of the support structure 20, protruding into the inner hollow.

Self expandable or balloon expandable transcatheter valve assemblies may be positioned inside the support structure 20.

Alternatively, or in addition, the support structure 20 may be an outer part of a valve assembly for transcatheter delivery. The unidirectional flow direction unit 800 may be an improved valve of the type of minimally-invasive heart valves, such as disclosed in U.S. Pat. No. 6,454,799 of Edwards Lifesciences, prosthetic valves for transluminal delivery, such as disclosed in U.S. Pat. No. 7,018,406 of Corevalve Inc., which are incorporated herein in their entirety for all purposes. In present embodiments, these known permanent valve assemblies are suitably modified for the present invention to be re-collapsible, and surrounded by an inflatable balloon 10.

Thus, a medical device having a unidirectional flow direction unit 800 and a surrounding inflatable balloon 10, and associated support structure 20, is provided. Applications for such a medical device are for instance medical procedures, where temporary creation of a temporary unidirectional flow is desired. The medical device may provide a simultaneous occlusion of an abnormal opening in the lumen wall.

An example for such a medical procedure comprises positioning the medical device in the venous system. For instance, the medical device may be positioned at a venous rupture in the venous system. A venous rupture may for instance occur in peripheral or central veins and needs medical treatment.

Another example is the positioning of temporary heart valves.

A method of deploying the medical device 1 at a branch site 100 by means of a medical system 2 as described above, will be given further below. Positioning at other openings than ostia to branch vessels is made correspondingly.

Figure 10B:
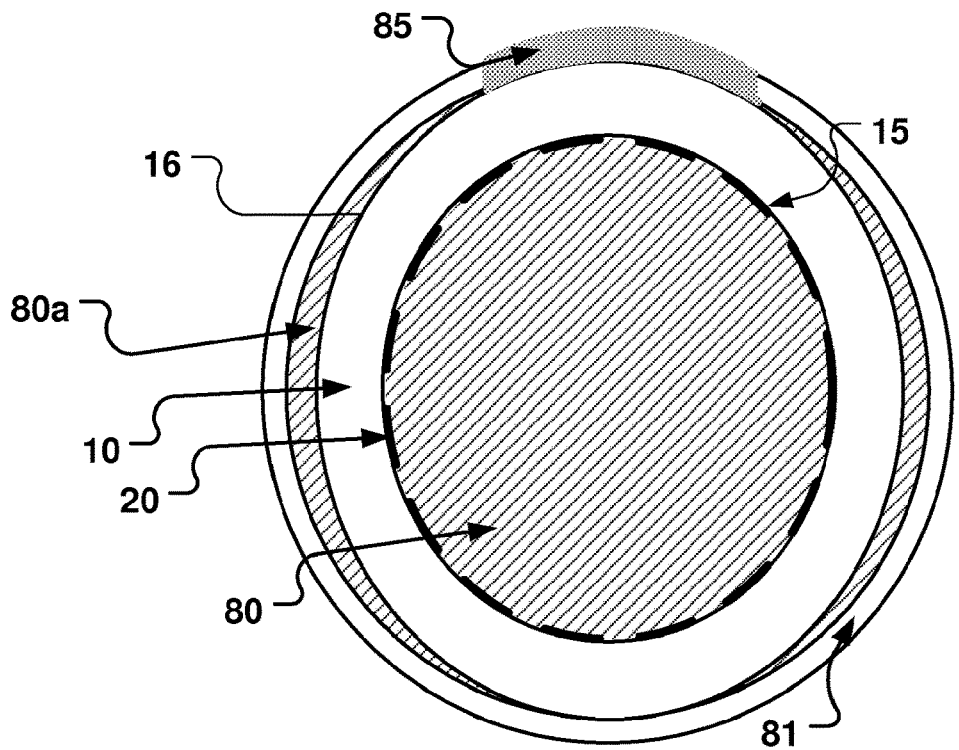
FIG. 10b is a cross sectional view through a medical occlusion device at an opening in a body lumen.

A medical device having an oval cross section is shown in FIG. 10b. Here, a fluid flow is also provided along the volume between the outer wall 16 and the lumen wall as illustrated by the hatched sections in the Fig.

The radial orientation of device in relation to the opening/weakening 85 provides a reliable sealing thereof, while the potential maximum fluid flow is increased by multiple flow passages. In addition, a risk of obstruction of the fluid flow in the main channel is reduced as redundancy of flow channels is provided. Furthermore, the additional flow channel 80a is not restricted, in contrast to the main lumen where a delivery unit is centrally arranged and webs or inflation lumen extend radially.

A kit 3 comprises at least two medical devices 1 of the type disclosed above. As illustrated in FIG. 5, a proximal medical device 1a and a distal medical device 1b are comprised in a kit 3. The aggregates of the medical devices 1a, 1b are spaced apart from each other and interconnected to each other by a fluid leakage tight interconnection unit 50 adapted to provide a through-flow of fluid between inner hollows of first balloons of the medical devices 1a, 1 b. The interconnection unit may extend past one or more openings in the lumen wall.

In the embodiment, the interconnection unit 50 is a tubular interconnection unit having a fluid tight tubular wall 51 between a proximal end and a distal end of the tubular interconnection unit. The tubular wall may be made of a membrane material. Suitable materials comprise polytetrafluoroethylene PTFE, commercially available as Gore-Tex®. Alternatively, or in addition, graft material may be provided that is reinforced. In this manner, the unit 50 is adapted to withstand radial outward expansion beyond a tubular shape of a desired maximum diameter. This diameter is for instance the outer diameter of the balloon 10, or the natural inner diameter of the main body lumen.

The proximal end of the tubular wall 51 is connected to a distal opening of the inner hollow 19 of the proximal medical device 1a. The distal end of the tubular wall 51 is connected to a proximal opening of the inner hollow of the distal medical device 1b. A fluid channel between the inner hollows of the two medical devices 1a, 1 b is provided. The medical devices 1a, 1b, upon inflation of first balloons thereof, provide a fluid tight positioning thereof against an inner wall of the main lumen and only allow a fluid flow through the inner hollow thereof. As the inner hollows are interconnected to each other by the tubular wall 51, a fluid flow into the opening 85 or branch vessel 90 is effectively prevented.

The tubular interconnection unit may have other cross sections than circular, e.g. oval, substantially flat, rectangular, etc.

The proximal medical device 1a is adapted to be positioned proximally of an ostium of the branch lumen into the main lumen. The distal medical device 1b is adapted to be positioned distally of the ostium. The tubular wall 51 is non-elastic and flexible and adapted to be arranged along the ostium, in the main lumen. It is preferably arranged at a distance from the ostium, without contacting tissue of the main lumen, ostium or branch lumen, as illustrated in FIG. 5. The outer diameter of the tubular wall 51 is preferably smaller than the natural inner diameter of the body lumen. Thus, it is avoided that debris is created, which can be flushed into the branch vessel upon removal of the medical devices.

The tubular wall 51 may comprise a reinforcement structure, such that pressure fluctuations therein substantially do not alter the tubular shape. In addition, a longitudinal substantially straight extension may thus advantageously be provided between the devices 1a and 1b.

Figure 7:
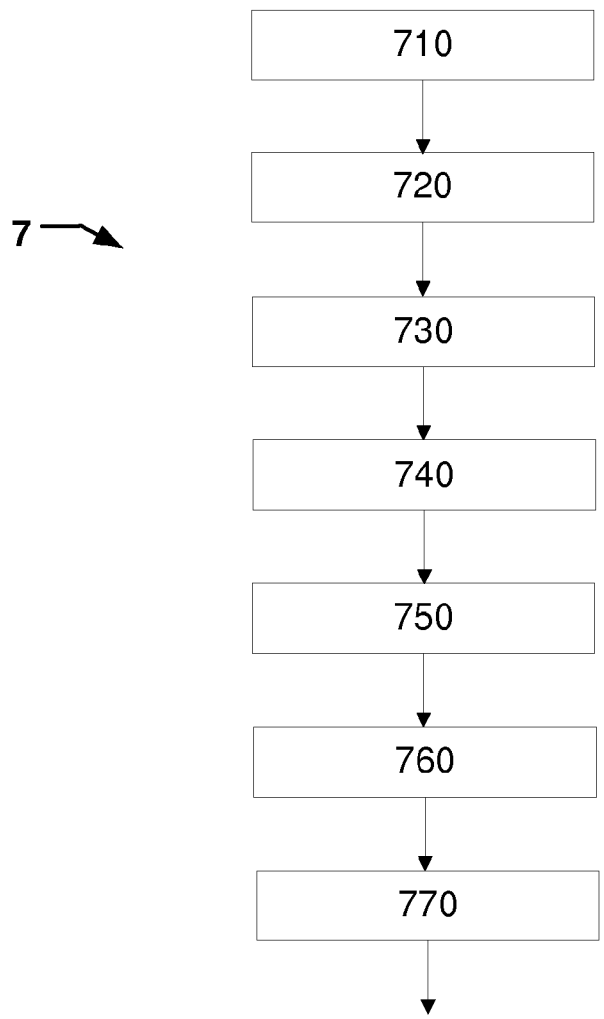
FIG. 7 is a flow chart illustrating a method of temporary occluding a fluid flow from a main lumen of a body into a branch lumen at a branch site inside the body.

Now turning to FIG. 7, a method 7 of temporary occluding a fluid flow from a main lumen of a body into a branch lumen at a branch site inside the body will be described. The method may be performed in an analogous way at other openings or structural tissue wall weakenings in a lumen than the described ostium of a branch vessel.

The method 7 for temporary occluding a fluid flow from a main lumen of a body into a branch lumen at a branch site inside the body comprises
transluminally delivering 710 a medical occlusion device in a collapsed state thereof to the branch site, and
expanding the medical occlusion device at the branch site at least partly by
inflating 720 a first inflatable balloon of the medical occlusion device substantially between a proximal end and a distal end thereof, and expanding a support structure, thus
appositioning 730 an outer wall of the first balloon at least partly to an inner wall of the main lumen at the branch site, and
keeping open 740 a passage of the fluid in the main lumen through a inner hollow of the first inflatable balloon interior of an inner wall thereof, and thus
substantially sealing off 750 a passage of the fluid into the branch lumen when the medical occlusion device is deployed at the branch site, and providing a longitudinal fluid flow through the inner hollow, and after an occlusion time and transluminally retracting the re-collapsed medical occlusion device from the branch site.

Further, the method comprises radially expanding 760 a support structure, longitudinally at least partly between the proximal end and distal end of the first balloon, at an inner wall of the first balloon, thus supporting a patency of the inner hollow by the support structure. The expanding 760 the support structure comprises inflating a second balloon at least partly arranged inside side inner hollow and the support structure, and expanding 770 the support structure to a diameter smaller than that of the main lumen. Alternatively, or in addition, the expanding 760 comprises self expanding the support structure. Alternatively, or in addition, the expanding 760 comprises controllably expanding the support structure by a catheter based wire from a proximal end of the catheter.

The expansion of the support structure is made to a diameter of the latter that is beyond a normal inflated inner diameter of the balloon, thus expanding the inner wall of the balloon radially outwards.

Inflating 720 the first balloon comprises inflating the first balloon to an outside diameter larger than an interior diameter of the main lumen.

The delivering 710 and retracting is performed by using a standard Seldinger technique and fluoroscopy. This makes the system user friendly and increases patient safety as a well established clinical method may be used with some modifications according to the invention.

The first and second balloon may be concurrently inflated via a common inflation lumen. Alternatively, the first and second balloon may be inflated independently via separate inflation lumina.

The first balloon and then the second balloon may be sequentially inflated.

In an embodiment, the method comprises positioning at least two medical occlusion devices at the branch site spaced apart from each other, and interconnecting the medical devices to each other by a fluid leakage tight interconnection unit adapted, thus providing a through-flow of fluid between inner hollows of first balloons of the medical devices.

The method comprises providing the through-flow through a fluid channel of a tubular interconnection unit having a fluid tight tubular wall between a proximal end and a distal end of the tubular interconnection unit, wherein the proximal end of the tubular wall is connected to a distal opening of the inner hollow of a proximal of the medical devices, and wherein the distal end of the tubular wall is connected to a proximal opening of the inner hollow of a distal of the medical devices in order to provide a fluid channel between the inner hollows.

The positioning at least two medical occlusion devices at the branch site spaced apart from each other comprises in the embodiment positioning a proximal medical occlusion device of the at least two medical occlusion devices proximally of an ostium of the branch lumen into the main lumen, and positioning of a distal medical occlusion device of the medical devices distally of the ostium, and arranging the tubular wall along the ostium, in the main lumen, and at a distance from the ostium, without contacting tissue of the main lumen, ostium or branch lumen.

In an embodiment, the lumen is a blood vessel, and the method comprises performing a surgery of an organ supplied with blood by the side branch lumen during at least a part of the occlusion period of time.

FIGS. 11a and 11b are side views of an embodiment of a medical occlusion device. In FIG. 11a a catheter 40 with a sheath 44 is shown having an aggregate of a support structure 20 and a balloon 10. This stent 20 is mounted to two extrusions. In addition to that, a balloon 10 with a separate extrusion line is mounted to the stent 20 as well. FIG. 11a shows the catheter 40 with a short sheath 44. FIG. 11b shows the tip section of this assembly. The stent and balloon are shown in the expanded and inflated state.

By advancing the first extrusion 310 into the second extrusion 320 at the proximal end of the catheter 40, the stent 20 is straightened. The stent 20 can be fixed in this position by screwing the male Luer lock 330 at the first extrusion 310 to the female Luer which is mounted to the second extrusion 320. A guide wire may be inserted as a supporting wire into the guide wire lumen, i.e. the second extrusion 320.

Then the stent 20 and the balloon 10 can be pulled back into the sheath tip. One may wrap the balloon 20 around the stent 10 to pull it back into the sheath 44, by pulling on all extrusions 310, 320 together.

Now the catheter 40 is ready for insertion into the body.

For expanding the aggregate of balloon and stent, the latter are advanced by pushing all the extrusions 310, 320 into the sheath 44. The Luer lock 330 is unlocked to expand the stent 20 as soon as the stent 20 is in the correct position.

By filling the balloon 10 with e.g. air or saline, side arms of the vessel are blocked. The maximal inflation volume that is pressed into the balloon, is previously defined to not exceed a threshold that may burst the balloon or collapse the sent. Otherwise the vessel could be blocked.

FIG. 12 is a side view of an embodiment of a medical occlusion device. A wire 45 manipulated from the proximal end of the catheter used for delivery of the medical device may provide the active expansion, e.g. by a relative movement of the support structure to the catheter sheath while being affixed to the latter in at least one point. Expanding a cage of a wire mesh initiated by a central control wire is an example for such a wire manipulation determining the degree of expansion of the support structure, like above with reference to FIG. 11b.

The aggregate 400 of balloon and support structure is elongated and collapsed by pushing the delivery wire distally. The wire may be locked in this position for delivery. By releasing the delivery wire, the aggregate expands to its natural form thanks to the elasticity of the support structure. From this natural relaxed form of the aggregate, the delivery wire is further drawn back in a relative movement to the catheter, thus actively further expanding the aggregate radially in the body lumen at the site of the opening or weakening in the lumen wall. The balloon is then inflated as described above.

The end sections of the balloon are cut in an oblique angle in order to facilitate insertion into the catheter and re-insertion into the latter upon withdrawal.

The balloon is made of two sheets that are welded to each other at the edges.

The occlusion device is neither released from the catheter nor released from the delivery unit; it remains affixed thereto at all times.

The device is positioned at the opening and then released from catheter in that position, and expanded and inflated into position, without further longitudinal re-location. The catheter sheath may e.g. be withdrawn in that position.

Figure 13A:
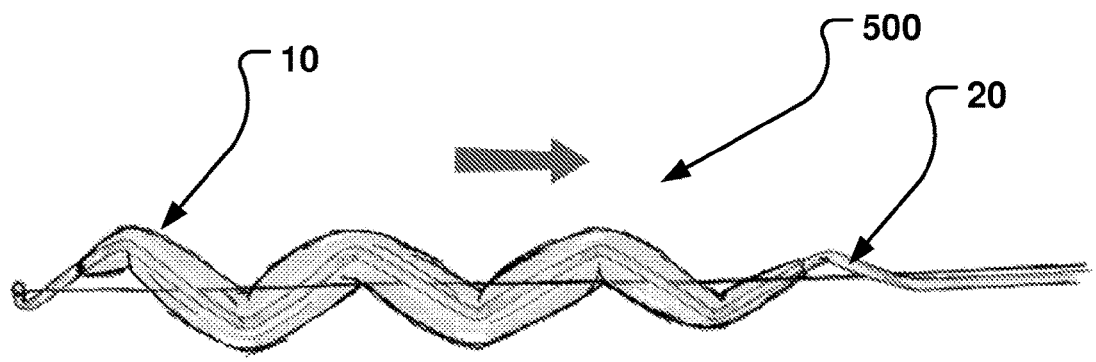
FIG. 13a is a lateral view of further medical occlusion device in an extended delivery shape.
Figure 13B:
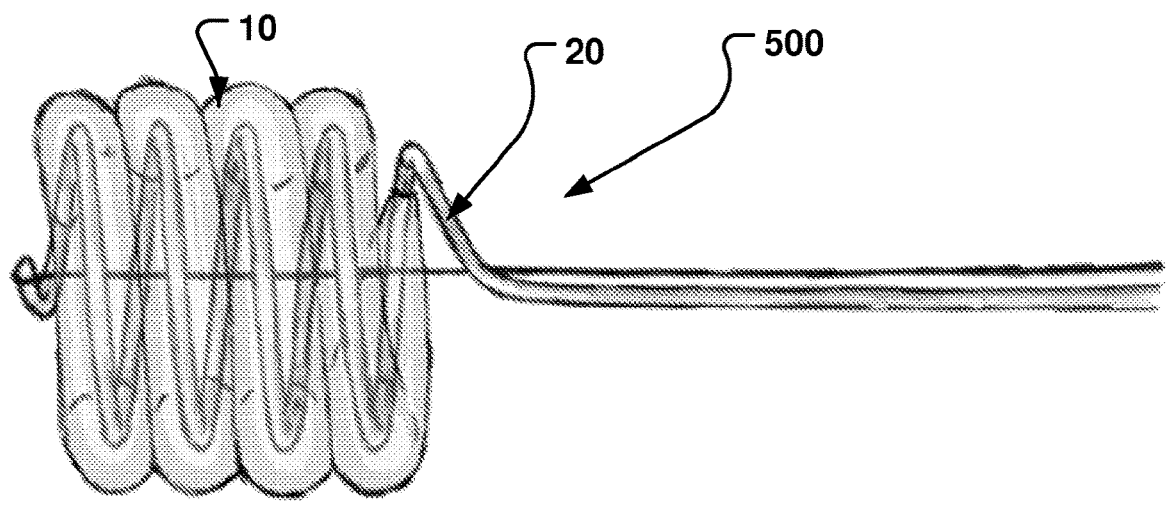
FIG. 13b is a lateral view of further medical occlusion device in an expanded shape.
Figure 13C:
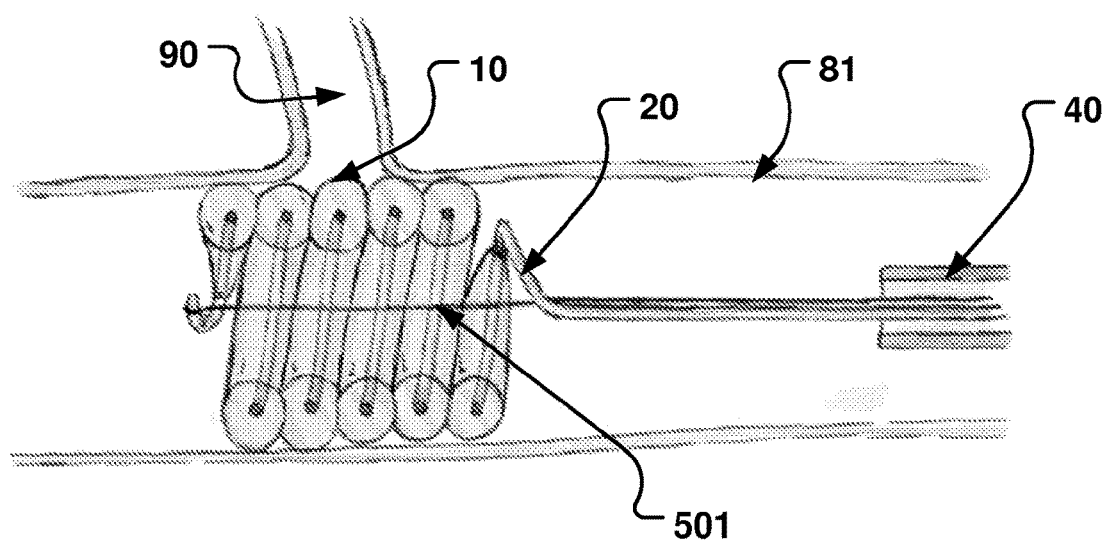
FIG. 13c is a cross sectional view of further medical occlusion device in an expanded shape, and inserted at an opening in a body lumen.

FIGS. 13a, 13b, 13c are two lateral views and a cross sectional view of further medical occlusion device 500 in an extended delivery shape, an expanded shape, and inserted at an opening in a body lumen, respectively.

The device is brought from the relaxed state (FIG. 13a) to the expanded helical shape by drawing a tether line 501 in the direction of the arrow in FIG. 13a.

When positioned at the opening, e.g. of a side lumen, the opening is blocked.

This embodiment has a small collapsed diameter and is in particular deliverable through narrow passages for delivery to the opening site.

Instead of a balloon 10, a soft, sponge like structure may be used. The structure may swell when it comes into contact with the body fluid in the lumen and thus increase the sealing effect.

Figure 14A:
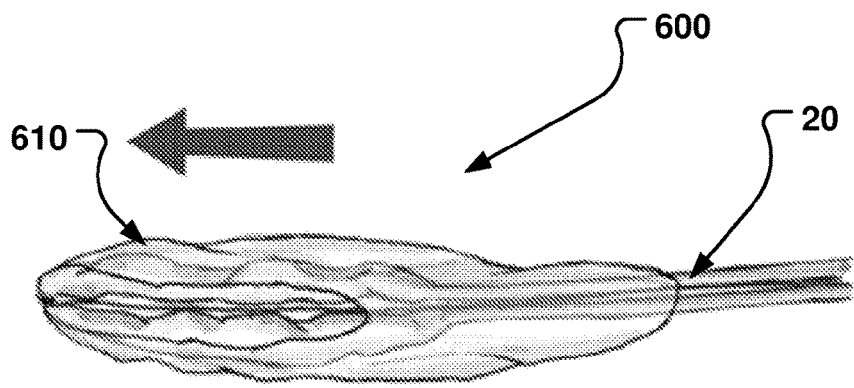
FIG. 14a is a lateral view of further medical occlusion device in an extended delivery shape.
Figure 14B:
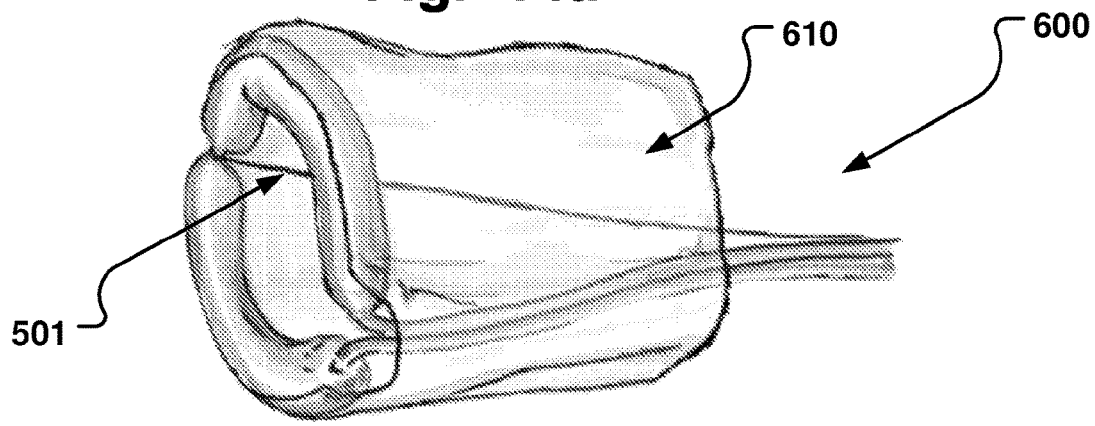
FIG. 14b is a lateral view of further medical occlusion device in an expanded shape.
Figure 14C:
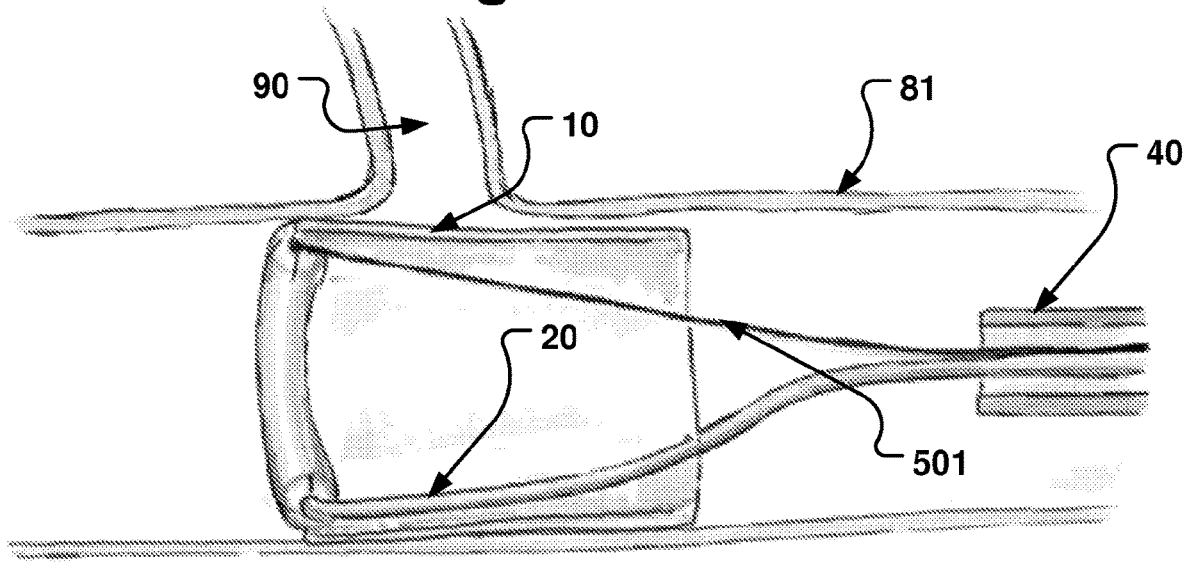
FIG. 14c is a cross sectional view of further medical occlusion device in an expanded shape, and inserted at an opening in a body lumen.

FIGS. 14a, 14b, 14c are two lateral views and a cross sectional view of further medical occlusion device 600 in an extended delivery shape, an expanded shape, and inserted at an opening in a body lumen, respectively.

The device 600 is if the windpipe design and is brought from the delivery state (FIG. 14a) to the expanded shape by pushing a tether line 501 in the direction of the arrow in FIG. 14a.

When positioned at the opening, e.g. of a side lumen, a flow into the opening is prevented, as the entire flow is diverted through the interior of the expanded device 600.

Instead of a balloon, a fluid tight fabric 610 is provided. This embodiment has a particular high through flow as the proximal end of the fabric has the same diameter as the distal end (which is oriented against the flow direction). The distal end has a soft cushion or inflatable balloon to increase sealing.

Figure 15A:
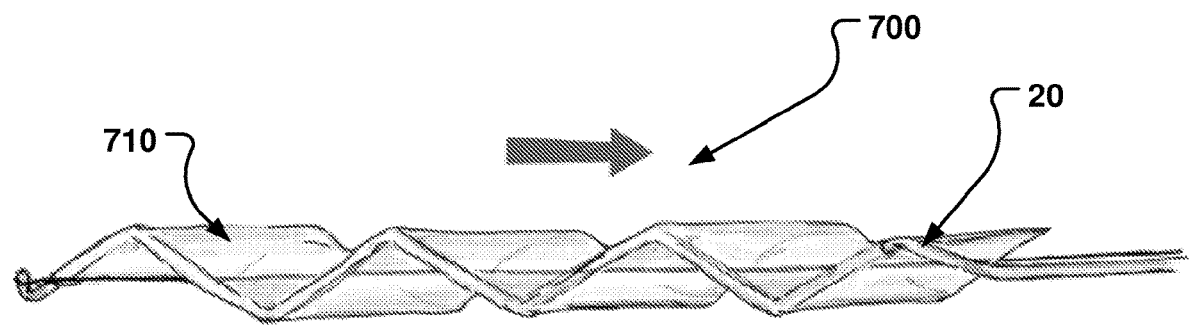
FIG. 15a is a lateral view of further medical occlusion device in an extended delivery shape.
Figure 15B:
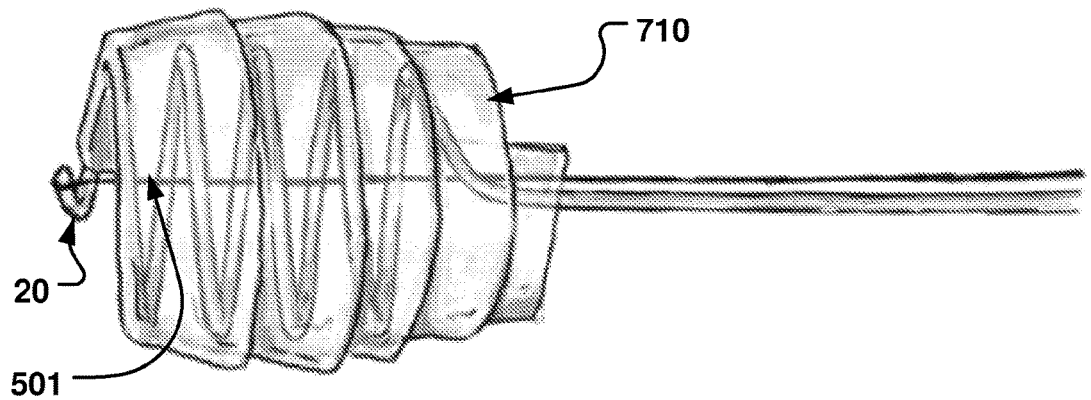
FIG. 15b is a lateral view of further medical occlusion device in an expanded shape; and, FIG. 15c is a cross sectional view of further medical occlusion device in an expanded shape, and inserted at an opening in a body lumen.
Figure 15C:
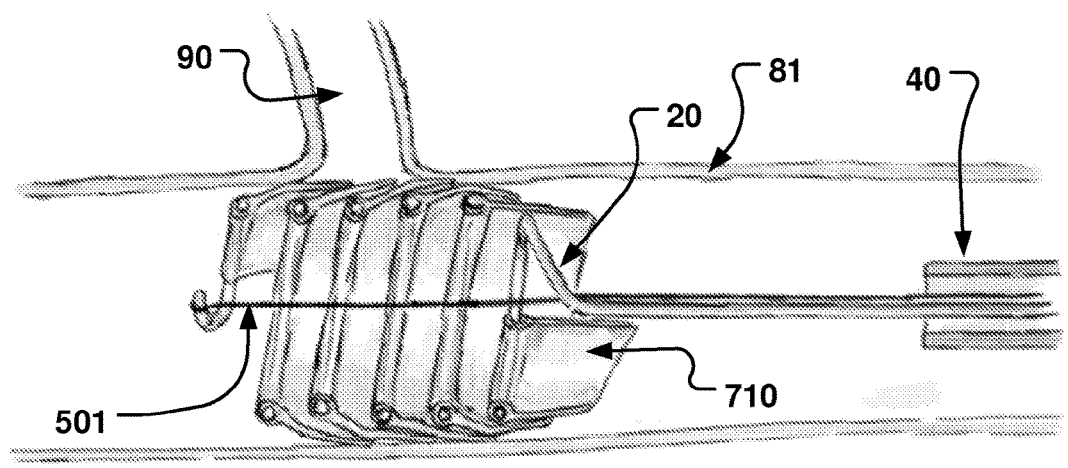

FIGS. 15a, 15b, 15c are two lateral views and a cross sectional view of further medical occlusion device 700 in an extended delivery shape, an expanded shape, and inserted at an opening in a body lumen, respectively.

The device 700 is brought from the relaxed state (FIG. 15a) to the expanded helical shape by drawing a tether line 501 in the direction of the arrow in FIG. 15a.

When positioned at the opening, e.g. of a side lumen, a flow into the opening is prevented, as the entire flow is diverted through the interior of the expanded device 600.

Instead of a balloon, a fluid tight fabric 610 is provided.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention as defined by the appended patent claims.

More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention as defined by the appended patent claims.

What is claimed is:

1. A method of cancer treatment, including
   delivering a cytostatic drug to a tumor infested organ having at least one blood vessel for a blood flow towards said organ,
   delivering a medical occlusion device having an inflatable balloon into said blood vessel or over an opening to said blood vessel,
   inflating said balloon after said delivering of said drug,
   shutting off said blood flow through said blood vessel to said organ by said inflating said balloon,
   upholding said shutting off temporary during a time period after said delivering of said cytosatic drug for letting said cytostatic drug become effective and not being washed out prematurely, and
   deflating said balloon after said time period.

2. A method of cancer treatment, including
   delivering a cytostatic drug to a tumor infested organ having at least one blood vessel for a blood flow towards said organ,
   delivering a medical occlusion device over a branch opening to said blood vessel,
   said medical device having extended delivery shape and an expanded helical shape,
   bringing said device to said expanded helical shape blocking said branch opening after said delivering of said cytostatic drug,
   shutting off said blood flow through said blood vessel to said organ by said blocking,
   upholding said shutting off temporary during a time period after said delivering of said cytosatic drug for letting said cytostatic drug become effective and not being washed out prematurely, and
   unblocking said opening after said time period by returning said medical occlusion device from said helical expanded shape to said extended delivery shape.

* * * * *